United States Patent
Bayer et al.

(10) Patent No.: US 10,226,581 B2
(45) Date of Patent: Mar. 12, 2019

(54) HAND-HELD DRUG INJECTION DEVICE AND DOSE SETTING LIMITER MECHANISM THEREFOR

(71) Applicant: SANOFI, Paris (FR)

(72) Inventors: Stefan Bayer, Würselen (DE); Daniel Berning, Baesweiler (DE); Philippe Blank, Düsseldorf (DE); Bjorn Wilden, Simmerath (DE); Wolfgang Pelzer, Kreuzau (DE)

(73) Assignee: Sanofi, Paris (FR)

( * ) Notice: Subject to any disclaimer, the term of this patent is extended or adjusted under 35 U.S.C. 154(b) by 478 days.

(21) Appl. No.: 14/783,190

(22) PCT Filed: Apr. 8, 2014

(86) PCT No.: PCT/EP2014/056982
§ 371 (c)(1),
(2) Date: Oct. 8, 2015

(87) PCT Pub. No.: WO2014/166904
PCT Pub. Date: Oct. 16, 2014

(65) Prior Publication Data
US 2016/0045673 A1    Feb. 18, 2016

(30) Foreign Application Priority Data
Apr. 10, 2013  (EP) .................................. 13163080

(51) Int. Cl.
*A61M 5/20* (2006.01)
*A61M 5/315* (2006.01)
*A61M 5/31* (2006.01)

(52) U.S. Cl.
CPC ...... *A61M 5/31553* (2013.01); *A61M 5/2033* (2013.01); *A61M 5/31583* (2013.01);
(Continued)

(58) Field of Classification Search
CPC ............ A61M 5/20; A61M 2005/2026; A61M 2005/314; A61M 5/315; A61M 5/31501;
(Continued)

(56) References Cited

U.S. PATENT DOCUMENTS 5,505,704 A * 4/1996 Pawelka ................. A61M 5/19
604/191
2006/0153693 A1   7/2006 Fiechter et al.
(Continued)

FOREIGN PATENT DOCUMENTS

CN           101909678         12/2010
WO      WO 2003/011374         2/2003
(Continued)

OTHER PUBLICATIONS

Rote Liste, "50. Hypophyses-, Hypothalamushormone, andere regulatorische Peptide u. ihre Hemmstoffe," Chapter 50, ed. 2008, 20 pages.
(Continued)

*Primary Examiner* — Bhisma Mehta
*Assistant Examiner* — William Frehe
(74) *Attorney, Agent, or Firm* — Fish & Richardson P.C.

(57) ABSTRACT

The present invention relates to a drive mechanism of a drug delivery device for dispensing of a dose of a medicament, the mechanism comprising: —a housing (20), —a piston rod (120) extending in an axial direction (1, 2) to operably engage with a piston (14) of a cartridge (12), —a drive sleeve (90) rotatably supported in the housing (20), at least partially enclosing the piston rod (120), the drive sleeve (90) is operably releasable from the piston rod (120) for setting of a dose and the drive sleeve (90) is operably engageable with the piston rod (120) for dispensing of the dose, —a dose limiting member (130) threadedly engaged with the drive sleeve (90), rotatably locked to the housing (20) and being
(Continued)

displaceable in axial direction (1, 2) in response to a rotation of the drive sleeve (90) relative to the piston rod (120), —at least one stop member (124) provided on the piston rod (120) to engage with the dose limiting member (130) for impeding a further displacement of the drive sleeve (90) relative to the piston rod (120), when a maximum dose configuration has been reached.

16 Claims, 16 Drawing Sheets

(52) U.S. Cl.
CPC .... *A61M 5/31585* (2013.01); *A61M 5/31593* (2013.01); *A61M 5/3157* (2013.01); *A61M 5/31541* (2013.01); *A61M 5/31558* (2013.01); *A61M 5/31563* (2013.01); *A61M 5/31575* (2013.01); *A61M 2005/202* (2013.01); *A61M 2005/2086* (2013.01); *A61M 2005/314* (2013.01); *A61M 2005/3126* (2013.01); *A61M 2005/3143* (2013.01); *A61M 2005/3152* (2013.01); *A61M 2005/3154* (2013.01); *A61M 2005/31508* (2013.01); *A61M 2205/581* (2013.01)

(58) Field of Classification Search
CPC ...... A61M 2005/3152; A61M 5/31525; A61M 5/31526; A61M 5/31528; A61M 5/31533; A61M 5/31548; A61M 5/31565; A61M 5/31576; A61M 5/31578; A61M 5/3158; A61M 5/31581; A61M 5/31583
See application file for complete search history.

(56) References Cited

U.S. PATENT DOCUMENTS

| | | | |
|---|---|---|---|
| 2009/0275916 A1* | 11/2009 | Harms | A61M 5/24 604/506 |
| 2010/0152671 A1* | 6/2010 | Raab | A61M 5/24 604/207 |
| 2011/0054412 A1 | 3/2011 | Eich et al. | |

FOREIGN PATENT DOCUMENTS

| | | |
|---|---|---|
| WO | WO 2006/089767 | 8/2006 |
| WO | WO 2007/017052 | 2/2007 |
| WO | WO 2007/030957 | 3/2007 |
| WO | WO 2009/06286 | 5/2009 |
| WO | WO 2009/132778 | 11/2009 |
| WO | WO 2012/084720 | 6/2012 |

OTHER PUBLICATIONS

International Preliminary Report on Patentability in International Application No. PCT/EP2014/056982, dated Oct. 13, 2015, 8 pages.
International Search Report and Written Opinion in International Application No. PCT/EP2014/056982, dated May 13, 2014, 13 pages.

* cited by examiner

A-A

B-B

B-B

HAND-HELD DRUG INJECTION DEVICE AND DOSE SETTING LIMITER MECHANISM THEREFOR

CROSS-REFERENCE TO RELATED APPLICATIONS

This application is a § 371 U.S. National State Application of PCT/EP2014/056982, filed Apr. 8, 2014, which claims priority to European Patent Application 13163080.8, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single and/or a last dose limiting mechanism.

It is a further aim to provide a drug delivery device comprising such a drive mechanism and comprising a cartridge sealed with a piston and being operably engaged with a piston rod of such drive mechanism. The drug delivery device should be rather easy and intuitive to handle.

SUMMARY OF THE INVENTION

In a first aspect a drive mechanism for a drug delivery device is provided for dispensing of a dose of a medicament. The drive mechanism comprises a housing preferably extending in an axial direction. Preferably, the housing is of substantially tubular or cylindrical shape that allows gripping and operating of the drive mechanism or of the entire drug delivery device by one hand of a user.

The drive mechanism further comprises a piston rod extending in axial direction and to operably engage with a piston of a cartridge containing the medicament to be dispensed by the drive mechanism. The cartridge comprises a piston, which, by means of a displacement in axial distal direction, serves to expel an amount of the medicament from the cartridge that corresponds to the axial displacement of the piston. The piston typically seals the cartridge in axial proximal direction.

The piston rod serves to displace the piston of the cartridge in an axial distal direction. The piston rod is therefore operable to apply distally directed thrust or pressure to the piston of the cartridge for displacing the same in distal direction for a predetermined distance that corresponds to a respective amount of the medicament to be dispensed.

The drive mechanism further comprises a drive sleeve which is rotatably supported in the housing and which is operably releasable from the piston rod for setting of a dose. Hence, during a dose setting procedure, the piston rod remains substantially stationary with respect to the housing while the drive sleeve, operably disconnected and released from the piston rod, is rotatable relative to the housing and hence relative to the piston rod.

However, for dispensing of the set dose, the drive sleeve is operably engageable with the piston rod. In a respective dose dispensing mode, piston rod and drive sleeve are operably engaged for that the drive sleeve may exert a driving force or driving momentum to the piston rod for driving the same in distal direction to displace the piston of the cartridge accordingly.

The drive mechanism further comprises a dose limiting member engaged with the drive sleeve such a way, that the dose limiting member is displaced in axial direction relative to the drive sleeve and/or relative to the piston rod when the drive sleeve rotates relative to the piston rod during a dose setting procedure. The dose limiting member is provided as a separate component of the drive mechanism and is directly engaged with the drive sleeve as well as with the piston rod.

Furthermore, the drive sleeve at least partially encloses the piston rod. Hence, the piston rod is axially guided through the drive sleeve. Piston rod and drive sleeve are preferably indirectly engageable. Hence, there is no direct mechanical interaction or contact between the drive sleeve and the piston rod. Transmission of a driving force or driving momentum from the drive sleeve to the piston rod is typically provided by another functional component of the drive mechanism.

The dose limiting member which is threadedly engaged with the drive sleeve is further rotatably locked to the housing. This way, the dose limiting member is prevented to rotate through the interaction with the housing. From this it follows, that the dose limiting member is displaceable in axial direction in response to a rotation of the drive sleeve relative to the piston rod and/or relative to the housing. Since the dose limiting member is rotatably locked to the housing, e.g. splined to the housing, the dose limiting member typically experiences a proximally-directed axial sliding displacement relative to the piston rod and/or relative to the drive sleeve when the drive sleeve is rotated in a dose incrementing direction.

Since the dose limiting member is operable to engage with the piston rod when a maximum dose configuration has been reached and since the dose limiting member is axially guided by the housing and is further threadedly engaged with the drive sleeve, the dose limiting member can be applied to a variety of differently configured drive mechanisms. Here, the dose limiting member does not have to be rotatably locked to the piston rod extending through the dose limiting member as well as through the drive sleeve.

Additionally, the drive mechanism comprises a stop member provided on the piston rod or integrated into the piston rod to engage with the dose limiting member. In this way, once a mutual abutment of stop member and dose limiting member has been reached, a further axial displacement of the dose limiting member relative to the piston rod and hence relative the drive sleeve during the dose setting procedure can be blocked.

The at least one stop member typically comprises a stop face to engage or to abut or to engage with the dose limiting member when a maximum dose configuration of the drive mechanism has been reached during a dose setting procedure. When the at least one stop and the dose limiting member mutually engage, the at least one stop serves to impede or to block a further dose incrementing displacement of the drive sleeve relative to the piston rod.

In general, the dose limiting member can be arranged inside the drive sleeve in a rather contactless configuration relative to the piston rod, which also extends therethrough. Internal friction of the drive mechanism can therefore be reduced. Moreover, also during dose setting, which is accompanied by a proximally-directed displacement of the dose limiting member relative to the drive sleeve and/or relative to the piston rod, the piston rod itself may remain completely unaffected or unimpaired by a dose setting displacement of drive sleeve and/or dose limiting member.

This beneficial effect is particularly attainable due to a substantially contactless arrangement of the piston rod relative to the dose limiting member and/or relative to the drive sleeve.

It may only up to reaching the maximum dose configuration that the piston rod for the first time operably engages with the dose limiting member to inhibit a further axial, preferably a proximally-directed displacement of the dose limiting member relative to the piston rod. Since the dose limiting member is threadedly engaged with the drive sleeve, a mutual stop configuration of dose limiting member and piston rod thereby effectively block a further rotation and dose incrementing displacement of the drive sleeve. Hence, a dose exceeding the amount of medicament remaining in the cartridge cannot be set.

In an embodiment, the dose limiting member is arranged radially between the drive sleeve and the piston rod. Preferably, the piston rod extends through a radial central portion of the drive sleeve as well as through a radial central portion of the dose limiting member. By arranging the dose limiting member almost completely inside the drive sleeve, a rather space saving arrangement of the dose limiting member can be attained. Preferably, the dose limiting member at least partially protrudes from the drive sleeve in axial direction in order to engage with the housing in a non-rotatable way.

According to another embodiment, the dose limiting member comprises a sleeve portion enclosing the piston rod. Typically, the dose limiting member with its sleeve portion is located inside the hollow drive sleeve. It is the sleeve portion of the dose limiting member which is threadedly engaged with an inside-facing wall of the drive sleeve.

In another embodiment, it is the sleeve portion of the dose limiting member that comprises an outer thread engaged with an inner thread of the drive sleeve. Therefore, the outer diameter of the sleeve portion of the dose limiting member substantially matches with an inner diameter of the drive sleeve. Due to the outside-facing threaded engagement with the drive sleeve, the dose limiting member may feature a comparatively large free inner diameter adapted to contactlessly receive the piston rod therethrough.

In another embodiment the dose limiting member further comprises a bracket portion extending in axial direction and at least partially protruding from a proximal end of the drive sleeve. The bracket portion is the portion of the dose limiting member, which at least partially protrudes from the proximal end of the drive sleeve irrespective of the rotational position of the drive sleeve and/or irrespective of the axial position of the dose limiting member relative to the drive sleeve.

Typically, the drive sleeve is rotatable in a dose incrementing direction until a maximum dose configuration is reached. In this maximum dose configuration, the bracket portion of the dose limiting member may almost entirely extend from the proximal end of the drive sleeve while the sleeve portion of the dose limiting member preferably remains completely inside the threaded portion of the drive sleeve. In said maximum dose configuration it is preferred, that the proximal end of the sleeve portion almost or substantially reaches the proximal end of the drive sleeve.

When rotated in the opposite direction, hence in a dose decrementing direction, e.g. during a dose dispensing procedure, the dose limiting member is operable to slide in distal direction until it reaches a distal stop inside the drive sleeve. In this configuration, which corresponds to a zero dose configuration at the end of a dispensing procedure, at least the proximal end of the bracket portion of the dose limiting member still protrudes from the proximal end of the drive sleeve. In this way, the bracket portion can remain in a locking engagement with a portion of the housing.

According to another embodiment, the bracket portion comprises two axially extending and parallel oriented branches that are mutually interconnected to form a closed frame structure to slidably receive a pin of the housing therein. Since the bracket portion forms a closed loop or a kind of a slit to receive a radially inwardly extending pin of the housing, the dose limiting member can be effectively secured against a rotation with the axial direction as axis of rotation.

A radial fixing of the dose limiting member is however obtained through the threaded engagement of the sleeve portion of the dose limiting member with a correspondingly-shaped inner thread of the drive sleeve.

In a further embodiment, the dose limiting member also comprises at least one radially inwardly extending protrusion engaged with a correspondingly-shaped groove of the piston rod. In this embodiment the dose limiting member is directly interlocked or engaged with both, the housing of the drive mechanism and with the piston rod. Even though the dose limiting member is now in permanent contact arrangement with the piston rod this embodiment may be beneficial in terms of a general design of the piston rod.

Typically, the piston rod comprises an outer thread to engage with an inner thread of a drive wheel. The drive wheel may selectively engage with the drive sleeve during a dose dispensing procedure. When threadedly engaged with a rotatable drive wheel, the piston rod has to be rotatably locked relative to the housing in order to experience a displacement in longitudinal distal direction under the action of a dose decrementing rotating drive wheel. Here, the dose limiting member may provide a rotational interlocking feature for the piston rod.

When the dose limiting member is rotatably engaged or rotatably locked to the housing and since the piston rod is splined or rotatably locked to said dose limiting member, the piston rod can be rotatably locked relative to the housing via the dose limiting member. In this aspect, the dose limiting member may provide a double function. In one aspect it provides an end of content functionality and in another aspect it serves to rotatably lock the piston rod relative to the housing for that a threaded engagement with a rotatable drive wheel is operable to advance the piston rod in distal direction during dose dispensing.

According to a further embodiment, the stop member, which may be integrally formed with the piston rod, may comprise a radially outwardly extending flange portion at a proximal end of the piston rod. In this way, the stop member may axially engage with a proximal rim of the sleeve portion of the dose limiting member when reaching the maximum dose configuration. Alternatively, the stop member of the piston rod may also be implemented as a proximal end of the axially extending groove of the piston rod. Here, the radially inwardly extending protrusion of the dose limiting member may axially abut with the end of the groove thereby inhibiting a further proximally-directed displacement of the dose limiting member relative to the piston rod when a maximum dose configuration has been reached.

According to a further embodiment the stop member of the piston rod comprises a crown wheel facing in distal direction and being designed to mate with a correspondingly geared proximal rim of the dose limiting member. Accordingly, also the proximal rim comprises a proximally extending crown wheel to engage with the distally-facing crown wheel of the stop member. By means of mutually corresponding crown wheels of stop member and dose limiting member, a well-defined axial engagement of piston rod and dose limiting member can be attained.

When the stop member of the piston rod comprises a crown wheel to mate with a correspondingly geared proximal rim of the dose limiting member it is of particular benefit when the piston rod is allowed to rotate relative to the dose limiting member and/or relative to the housing during dose dispensing. In particular it is conceivable, that the drive wheel is splined, hence rotatably interlocked to the piston rod. Then, a dose decrementing rotation of the drive wheel serves to rotate the piston rod accordingly. Here, the piston rod may be threadedly engaged with the housing, thereby experiencing a distally-directed and dose dispensing displacement when the drive wheel and hence the drive sleeve are rotated in the dose decrementing direction.

When reaching a maximum dose configuration it is intended, that piston rod and dose limiting member are displaceable in distal direction together. When reaching a zero dose configuration at the end of a respective limited dose dispensing procedure, the dose limiting member and the piston rod remain precisely engaged by means of the mutually corresponding crown wheels. In order to provide a simultaneous and synchronous distally-directed displacement of piston rod and dose limiting member it is of particular benefit, when the outer threads of piston rod and dose limiting member comprise substantially identical leads.

The stop member of the piston rod may also be even or flat shaped in distal direction, in particular when the piston rod and the dose limiting member are subject to a purely axially directed displacement.

In a further embodiment, the drive sleeve is axially displaceable in distal direction against the action of a spring element. The spring element is typically sandwiched between a proximal rim of the drive sleeve and a drive wheel rotatably engaged with the piston rod. The drive wheel is preferably axially secured in the housing of the drive mechanism while the drive sleeve is axially displaceable in distal direction relative to the drive wheel.

In particular, the drive sleeve typically disengages from the drive wheel under the action of the spring element. Then, the drive mechanism is in dose setting mode since a dose setting rotational displacement of the drive sleeve is substantially effectless on the drive wheel and/or on the piston rod. Preferably, the drive sleeve is rotatable in a dose incrementing direction against the action of another spring element, by way of which manually applied torque or energy provided by a user of the device can be stored and saved in or by the drive mechanism.

Due to a distally-directed displacement of the drive sleeve relative to the drive wheel, a torque or momentum-transmitting engagement of drive sleeve and drive wheel can be obtained. Additionally, the drive sleeve is then operably coupled with the additional spring element, e.g. by way of a clutch or ratchet member, thereby experiencing a spring-based driving force that serves to rotate the drive sleeve in dose decrementing direction. Switching of the drive mechanism from dose setting mode into dose dispensing mode comes along with a rotational release of the drive sleeve together with a torque transmitting- or rotational interlocking of the drive sleeve with the drive wheel. Preferably, the torque transmitting engagement of drive sleeve and drive wheel is obtained before a spring-based driving force is released to set the drive sleeve in dose dispensing rotation.

In a further embodiment, the drive wheel is threadedly engaged with the piston rod. Hence, the drive wheel comprises a central through opening featuring an inner thread mating with an outer thread of the piston rod. Even though the drive wheel is axially fixed in the housing, a rotation of the drive wheel then leads to a distally-directed displacement of the piston rod when the piston rod is rotatably locked to the housing, either directly or via the dose limiting member, as described above.

In a further embodiment, the drive sleeve comprises a crown wheel portion at a distal end face to mate with a correspondingly-shaped crown wheel portion of the drive wheel. Preferably, the axial expansion or extension of the crown wheel portions of drive sleeve and drive wheel is such, that already an initial and limited distally-directed displacement of the drive sleeve relative to the drive wheel is already sufficient to provide a torque transmitting engagement of drive sleeve and drive wheel.

When displacing the drive sleeve further in distal direction, the torque transmitting engagement of drive wheel and drive sleeve can be sustained. However, this consecutive distally-directed displacement of the drive wheel may serve to disengage a ratchet mechanism by which the drive sleeve is selectively interlocked to the housing.

In still another embodiment, the proximal rim of the drive sleeve is geared with a pinion of a drive spindle rotatably supported in the housing in a dose incrementing direction against the action of a spring element. Here and in particular in the dose dispensing mode, the drive sleeve is driven by the spring supported drive spindle, which is geared with the geared rim of the drive sleeve. The drive spindle is typically threadedly engaged with another drive member, which is threadedly engaged with the drive spindle and which is axially and slidably displaceable relative to the housing.

Here, the drive member may be directly engaged with a compression spring or with a helical spring. A helical spring is particularly adapted to directly induce a dose decrementing rotation onto the drive spindle whereas a compression spring to be compressed in axial direction may engage with an axially displaceable drive member threadedly engaged with the drive spindle to form a spindle gear.

Moreover and according to another embodiment, the drive wheel also comprises a geared rim at its outer circumference engaged with a ratchet member of the housing which is operable to generate an audible click sound when the drive wheel rotates in a dose dispensing, hence in a dose decrementing direction. Moreover, the ratchet member of the housing is also operable to impede a rotation of the drive wheel in the opposite, hence dose incrementing direction. In this way it can be effectively assured, that the piston rod is only and exclusively displaceable in distal direction during dose dispensing. A proximally-directed displacement of the piston rod relative to the housing is therefore effectively impeded.

According to another aspect, the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a reusable or in case of a disposable drug delivery device, respectively. Consequently, the drug delivery device comprises a cartridge holder to receive and to accommodate a cartridge filled with the medicament.

Apart from that, the drug delivery device and the drive mechanism may comprise further functional components, such like a dose injection member, by way of which a user may trigger and control the drug delivery device and its drive mechanism for dispensing of a dose of the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N- palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, embodiments of the invention will be described by making reference to the drawings, in which.

DETAILED DESCRIPTION

Figure 1:
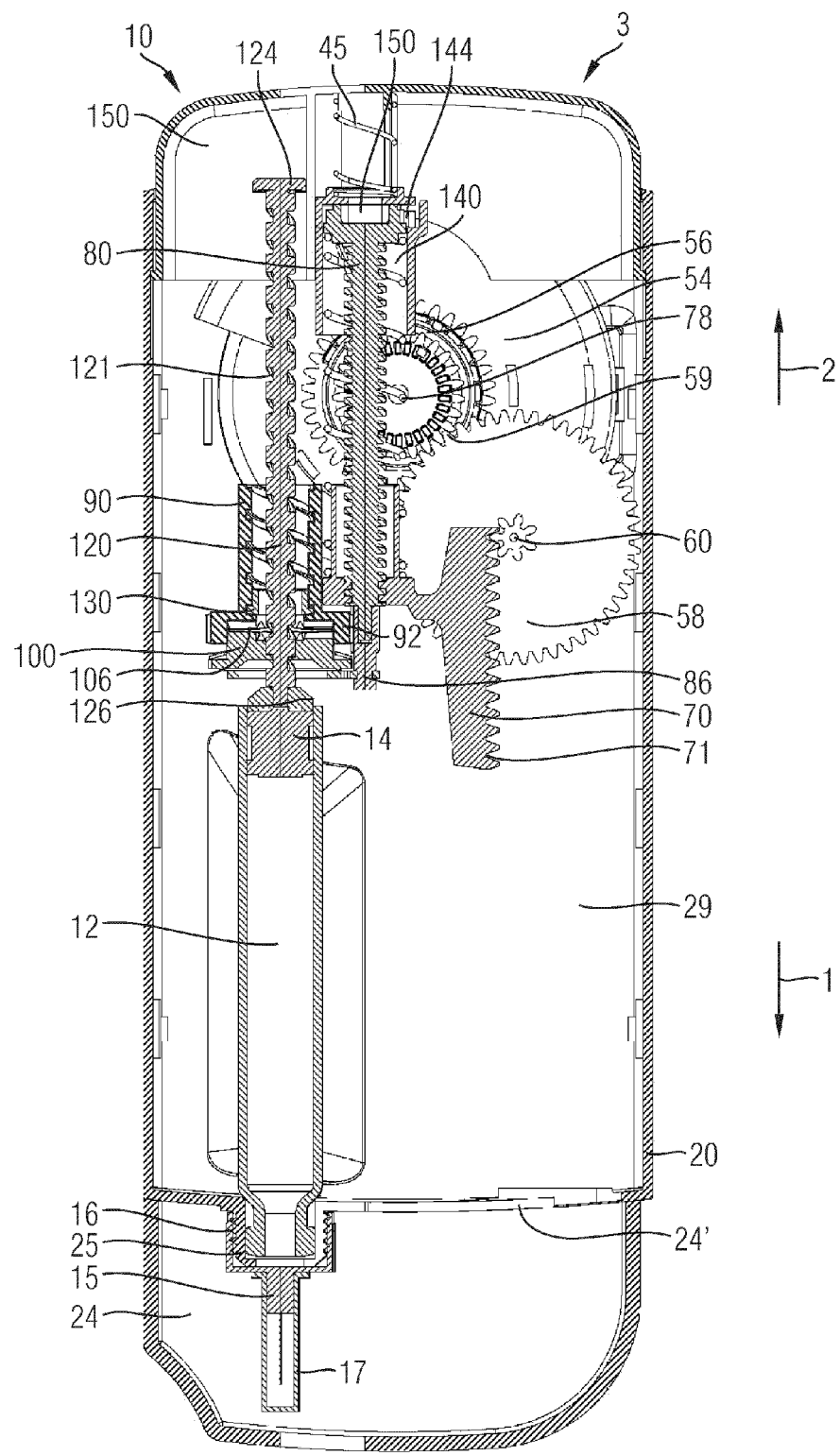
FIG. 1 schematically illustrates a front view of the drug delivery device.
Figure 2:
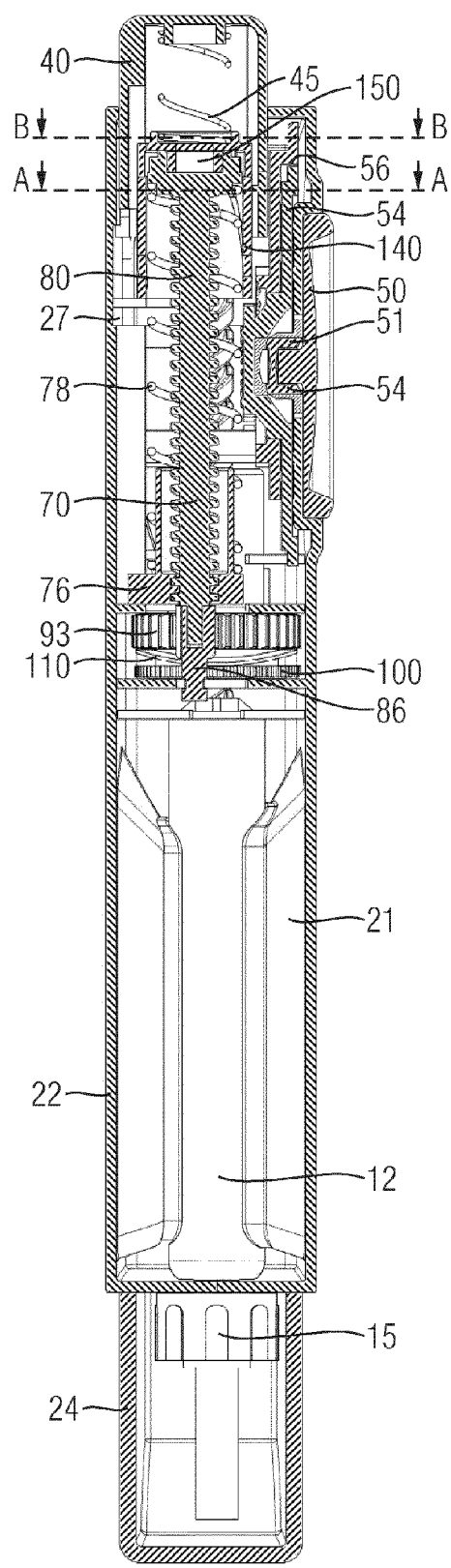
FIG. 2 shows a side view of the drug delivery device.
Figure 3:
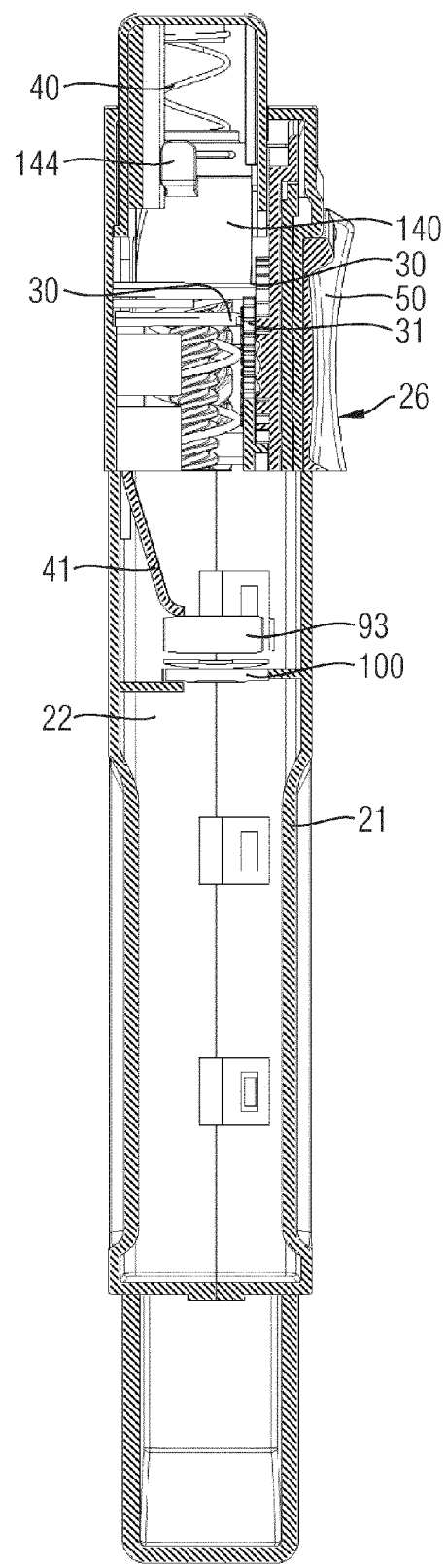
FIG. 3 shows another side view as seen from the opposite side compared to FIG. 2.

As illustrated in FIGS. 1 and 2 the drug delivery device 10 comprises a rather rectangular or cubic-shaped housing 20 comprising an upper housing portion 21 and a lower housing portion 22. In the present embodiment, the upper housing portion 21 may serve as a mounting base to assemble the components of the drive mechanism 3 thereon. The lower housing portion 22 may then serve as a cover, which preferably stabilises and keeps the various components of the drive mechanism 3 at their positions. However, the roles of upper and lower housing portions may also be interchanged in alternative embodiments.

The rectangular shape of the housing 20 is particularly adapted to take and to clasp the device 10 by one hand of a user. The drug delivery device 10 therefore comprises an elongated shape extending in axial direction. In the present context, the axial distal direction is denoted with reference number 1 and the opposite proximal direction is denoted with reference number 2. The housing 20, in particular both of its halves 21, 22, comprises a cartridge window 23.

The cartridge window 23 may comprise a recess in the upper and/or lower housing portion 21, 22 and may be at least partially transparent to allow visual inspection of a filling level of a cartridge 12 assembled inside the housing. The distal end of the housing 20 is further provided and protected by a removable cap 24. The cap 24 may positively engage with a distal end of upper and lower housing portions 21, 22 in order to protect a threaded socket 25 formed by upper and lower housing portions 21, 22.

Figure 6:
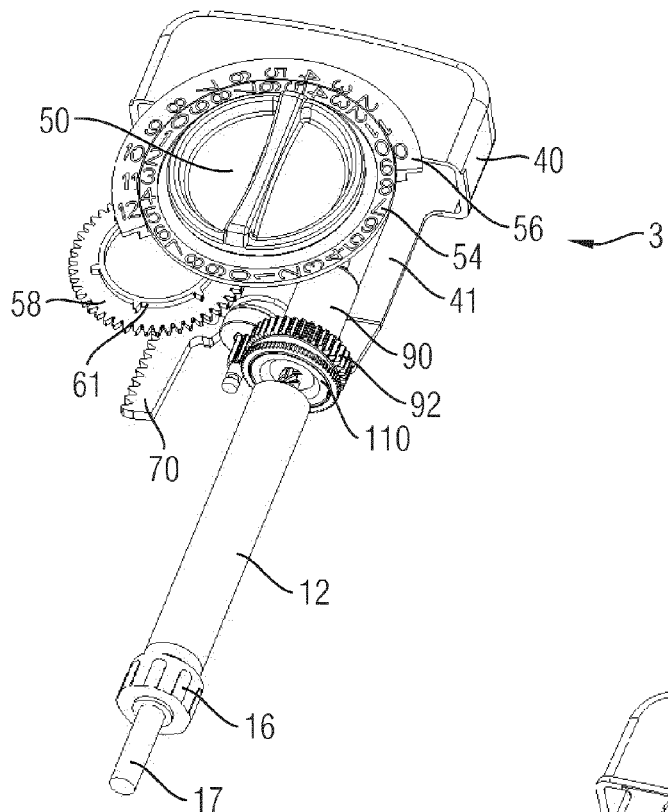
FIG. 6 shows a perspective isolated view of a dose indicating arrangement as seen from the front.
Figure 7:
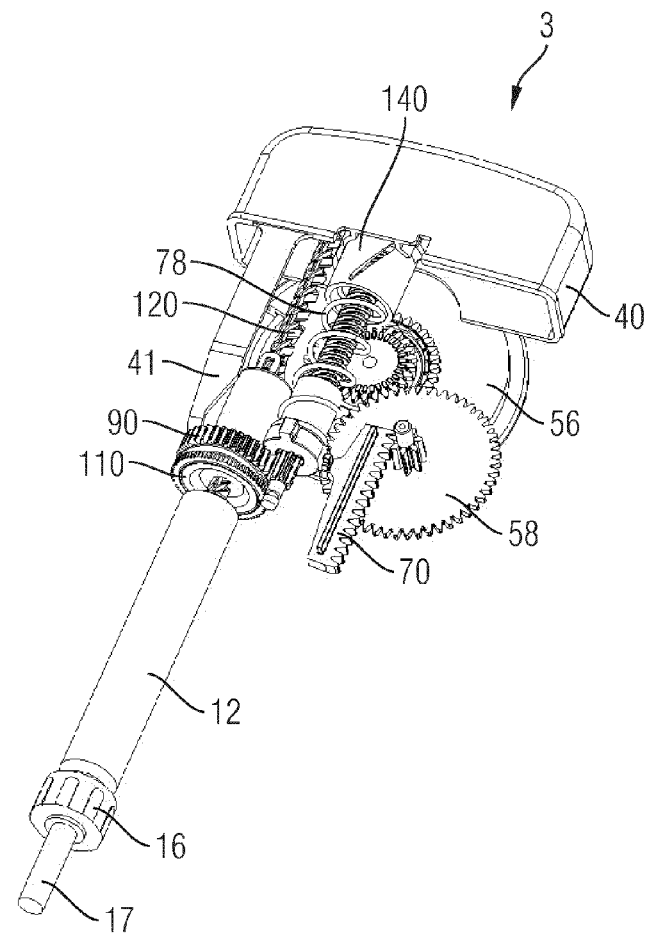
FIG. 7 shows the dose indicating arrangement according to FIG. 6 from the back side.
Figure 8:
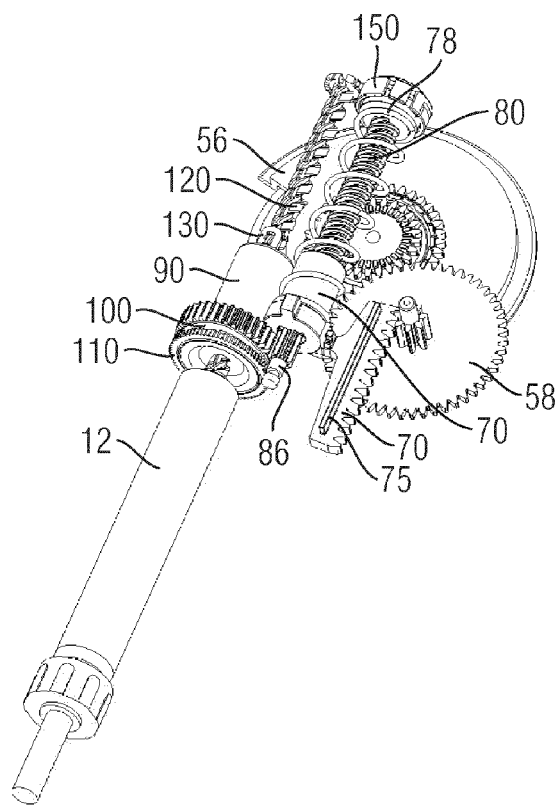
FIG. 8 shows an enlarged view of the dose indicating and dose setting arrangement according to FIG. 7.

The threaded socket 25 is adapted to receive a needle assembly 15, in particular a cup-shaped needle hub 16 providing a double-tipped injection needle. In the various Figures, in particular in FIGS. 1, 2 and in FIGS. 6 and 7, the needle assembly 15 is illustrated with a needle cap 17, which is to be removed from the needle assembly 15 prior to conducting a dose dispensing procedure. The cartridge 12 to be fixed in the housing 20 comprises a tubular-shaped barrel filled with a medicament to be dispensed by the drug delivery device 10.

The barrel is sealed in proximal direction 2 by means of a piston 14, which is slidably disposed in axial direction 1, 2 inside the barrel of the cartridge 12. The piston 14 of the cartridge 12 is operably engageable with a piston rod 120. The piston rod 120 of the drive mechanism 3 is operable to apply distally-directed thrust or pressure to the piston 14 in order to drive the same in distal direction 1. In this way, a fluid pressure may build up inside the cartridge 12.

When the distal dispensing end of the cartridge 12 is connected with the needle assembly 15 in such a way, that a proximally extending tipped portion of the needle penetrates a distally-located seal of the cartridge, e.g. a septum, a predefined amount of the medicament can be expelled from the cartridge 12 via the needle assembly 15 and into biological tissue.

Figure 5:
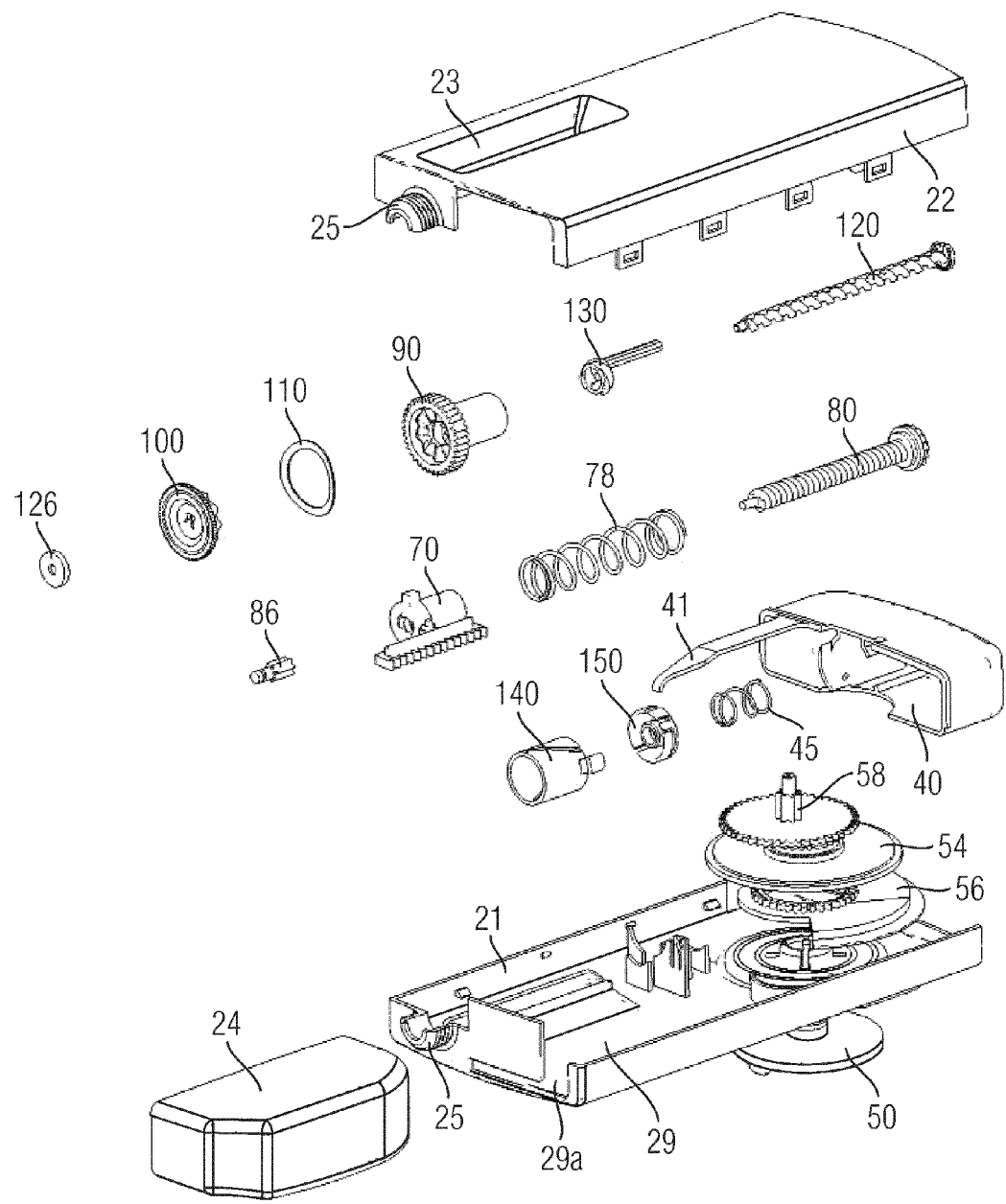
FIG. 5 is an exploded view of the components of the drive mechanism.

As indicated in FIG. 1, the housing 20 comprises a compartment 29 adapted to receive the protective cap 24. For this purpose, the distal end face of the housing 20 comprises a slit 29a as indicated in FIG. 5 allowing to slidably receive the protective cap therein. Here, the slit 29a may serve as a hinge to pivot and to slidably receive the cap 24 when the device is in use. In this way, the cap 24 is non-removably attached to the housing 20 and cannot get lost.

In the following, setting of a dose is described.

For setting of a dose, the user typically takes or clasps the housing 20 in one hand and starts to rotate, in particular to dial a dose setting member 50 located in the upper housing portion 21. The dose setting member 50 as illustrated in detail in FIG. 10 comprises a circular-shaped button comprising an outer rim and a central gripping bar 52 extending across the disc-shaped dose setting member 50. The gripping bar 52 divides the dose setting member 50 into two recesses allowing for an intuitive and easy gripping thereof.

Figure 10:
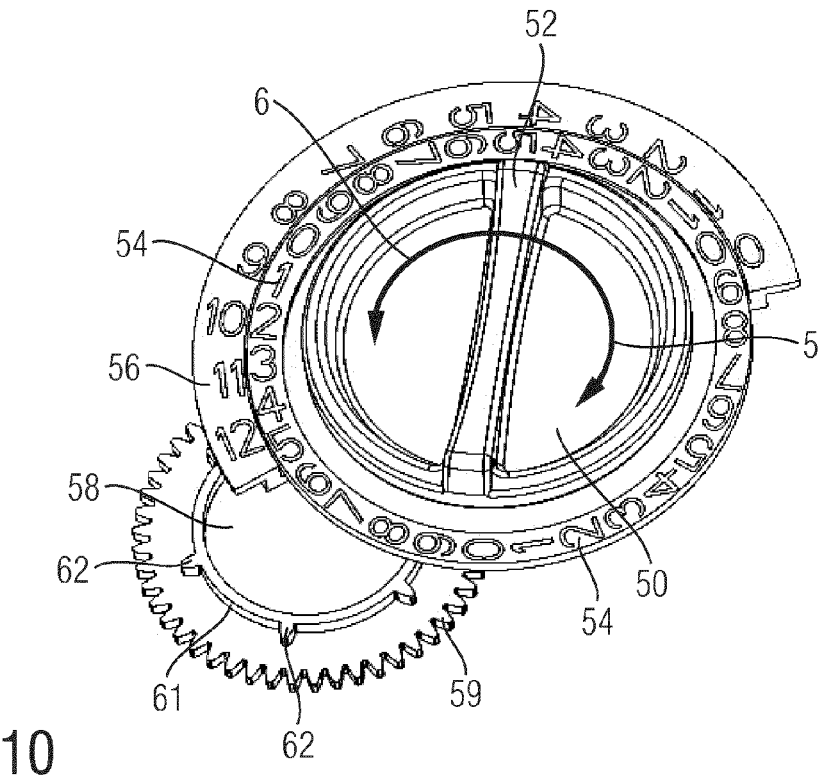
FIG. 10 is an isolated view of the interleaved first and second dose indicating wheels as seen from the front.
Figure 11:
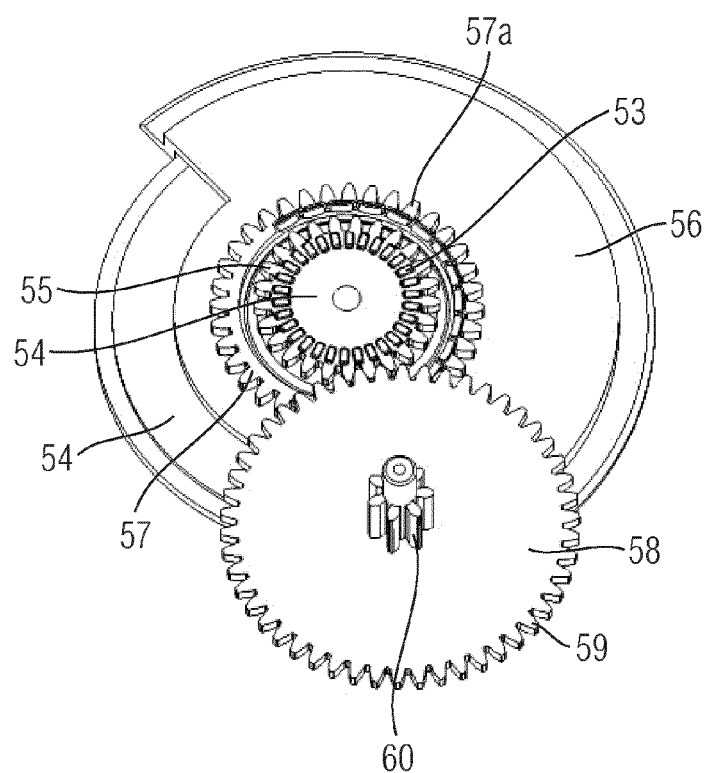
FIG. 11 shows the wheels according to FIG. 10 from the back side.

As indicated by the arrows in FIG. 10, the dose setting member 50 can be rotated either clockwise 5, e.g. in a dose incrementing way or counter-clockwise, e.g. in a dose decrementing way for incrementing or decrementing a dose to be dispensed by the drug delivery device 10. The dose setting member 50 is directly coupled to a dose indicating arrangement as illustrated in FIGS. 10 and 11. The dose setting member 50 as illustrated in cross-section of FIG. 12 is rotatably coupled with a dose indicating wheel 54.

Figure 12:
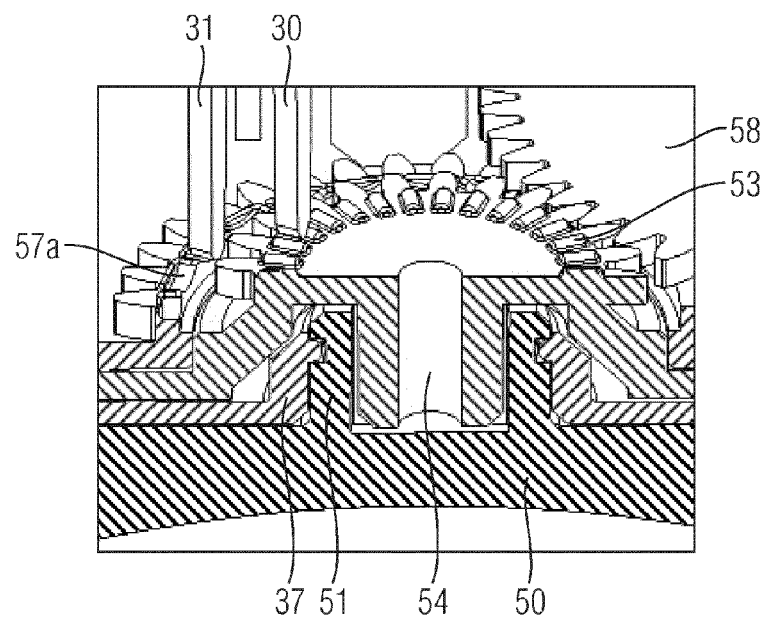
FIG. 12 shows a perspective and partially cut view of the dose indicating wheels assembled in the housing.

As indicated in FIG. 12, the dose indicating wheel 54 comprises an axially extending shaft received in a correspondingly-shaped receptacle of the dose setting member 50. Even though not illustrated, the shaft and the receptacle are splined. Shaft and receptacle of the dose indicating wheel 54 and the dose setting member 50 comprise at least one protrusion engaged with a correspondingly-shaped groove.

As further illustrated in FIG. 12, the receptacle 51 of the dose setting member 54, in particular its sidewall is positively engaged with an inwardly extending fixing rim of the housing 20, thereby fixing the dose setting member 50 in axial direction relative to the housing 20 but allowing the dose setting member 50 to rotate in either direction relative to the housing 20.

The dose indicating wheel 54 serves as a first dose indicating wheel and comprises a series of dose indicating numbers at its outer circumference as illustrated in FIG. 10. Here, the dose setting member 50 and the first dose indicating wheel 54 are coaxially aligned. The dose indicating wheel 54 may feature an outer rim substantially enclosing the outer circumference of the dose setting member 50.

Figure 25:
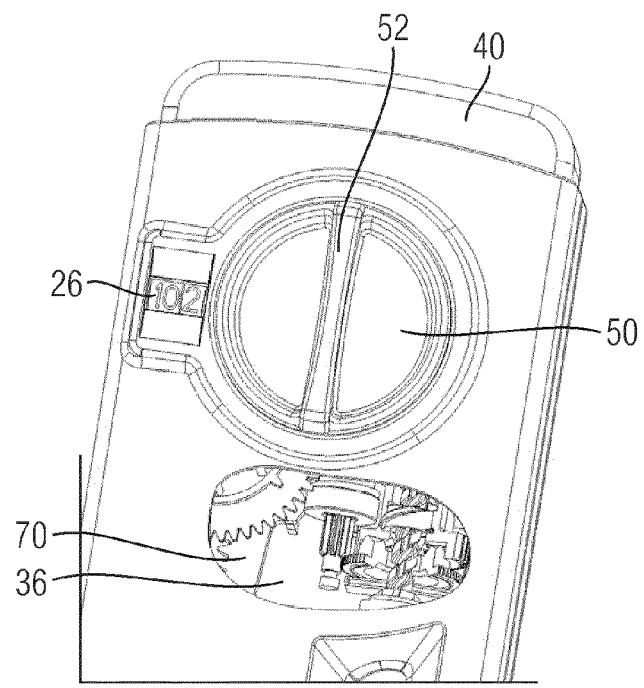
FIG. 25 shows a partially cut view of the assembled drug delivery device.

Due to the splined and direct engagement of the dose setting member 50 and the first dose indicating wheel 54, a rotation of the dose setting member 50 in either direction directly transfers to a respective rotation of the first dose indicating wheel 54. As a consequence, a respective number printed on a side of the dose indicating wheel 54 shows up in a dose indicating window 26 of the housing 20 as illustrated in FIG. 25.

The first dose indicating wheel 54 comprises a sprocket 55 to engage with an outer geared rim 59 of a gear wheel 58. The gear wheel 58 as illustrated in FIG. 11 comprises a further sprocket or pinion 60 axially offset from the geared rim 59 of the gear wheel 58. As will be explained later on, the sprocket 60 is engaged with a toothed rack portion 71 of a drive member 70.

On the side opposite to the sprocket 60 the gear wheel 58 comprises a rim structure 61 featuring isolated and separated cogs 62. Said cogs 62 are operable to engage with a geared rim 57 or sprocket of a second dose indicating wheel 56. As illustrated in FIGS. 10 and 11, the second dose indicating wheel 56 provides a second series of ten digit representing numbers of 10, 20, 30 and so on. By means of the isolated and circumferentially separated cogs 62, a stepwise incrementing rotation of the second dose indicating wheel 56 can be attained when the first dose indicating wheel 54 rotates.

In effect, by means of the two dose indicating wheels 54, 56 all numbers of for instance between 0 and 120 can be illustrated in the dose indicating window 26 of the housing 20. Implementation of the two interleaved dose indicating wheels 54, 56 allows for a rather large scale display so that even persons suffering impaired vision are enabled to read the illustrated numbers.

The first and the second dose indicating wheels 54, 56 further comprise a crown wheel 53, 57a engaging with clicking members 31, 30 provided on the inside of the oppositely disposed housing portion 21. As illustrated in FIG. 12, an inwardly extending pin-shaped clicking member 31 engages with a crown wheel 53 located on a side face of the first dose indicating wheel 54. Correspondingly also the second dose indicating wheel 56 comprises a crown wheel 57a to mate with a correspondingly-shaped clicking member 30 of the housing 20.

Mutual engagement of the first and second dose indicating wheels 54, 56 with respective clicking members 31, 30 provides an audible click sound when the dose setting member 50 is rotated either in dose incrementing direction or in dose decrementing direction. In this way, an audible feedback can be provided to the user when dialing the dose setting member 50 in either direction.

As illustrated for instance in FIGS. 7, 8, 19 and 20 the centrally-located sprocket 60 of the gear wheel 58 meshes with a toothed and elongated rack portion 71 of a drive member 70. The drive member 70 is axially displaceable relative to a drive spindle 80 extending therethrough. The drive member 70 comprises a sleeve portion 72 to receive the drive spindle 80, which is axially fixed in the housing 20 by means of a bearing 33 as for instance illustrated in FIGS. 13 and 20.

Figure 15:
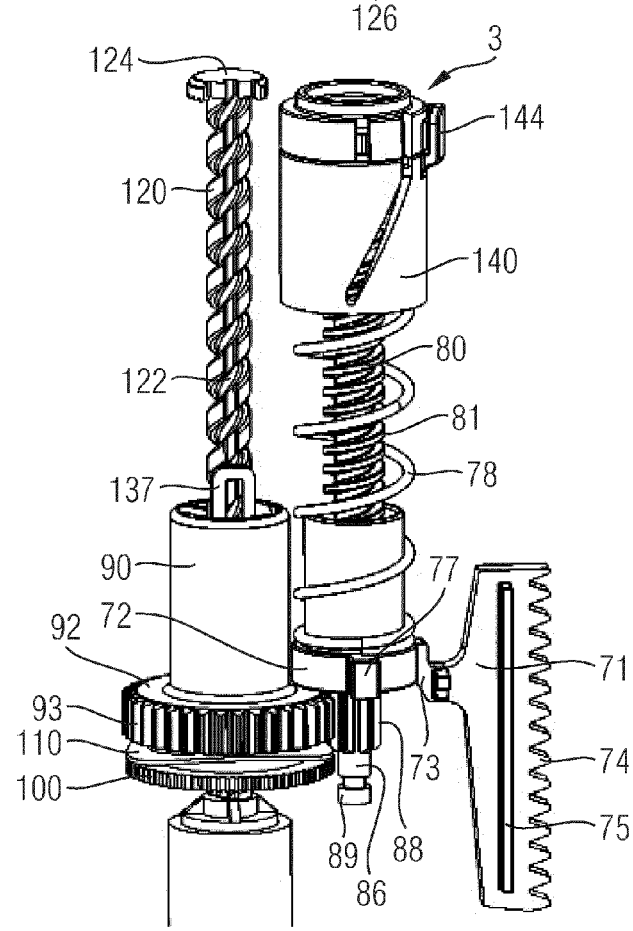
FIG. 15 is a perspective view of the mutual engagement of drive sleeve, drive spindle and drive member.

As illustrated in detail in FIG. 15, the toothed rack portion 71 is connected with the sleeve portion 72 via an interconnecting bar 73. The toothed rack portion 71 therefore radially outwardly extends from the sleeve portion 72 of the drive member 70. The drive member 70 is axially displaceable relative to the drive spindle 80 and relative to the housing 20 against the action of a spring element 78.

As illustrated in FIG. 15, the spring element 78 helically winds around the drive spindle 80. The spring element 78 is preferably designed as a compression spring and can be tensioned by an upward, hence proximally-directed displacement of the drive member 70 relative to the drive spindle 80. As further illustrated in FIG. 15, the sleeve portion 72 of the drive member 70 comprises a radially outwardly extending rim 76 at its distal end, which serves as a distal stop for the spring element 78.

Figure 13:
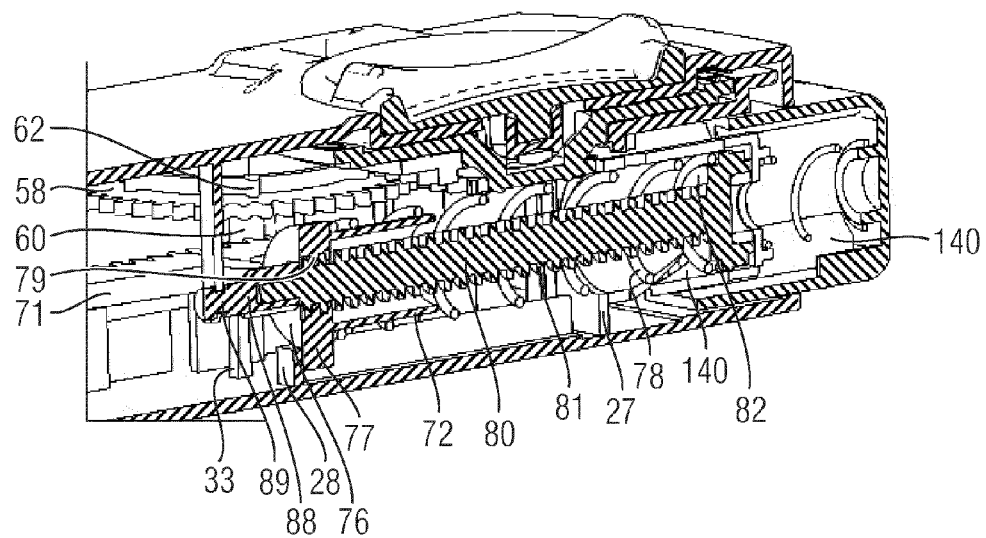
FIG. 13 shows a partially cut and perspective view of the drive spindle arranged in the housing.

Furthermore, the rim 76 comprises a radially outwardly extending protrusion 77 by way of which the drive member 70 can be axially guided relative to the housing 20. Moreover, the protrusion 77 may act as an axial stopper for the drive member 70. As shown in FIG. 13, the housing 20 comprises a proximal stop 27 and a distal stop 28 that are operable to engage with the radially outwardly extending protrusion 77 of the drive member 70. In this way, axial displacement of the drive member 70 relative to the housing 20 can be delimited in distal direction 1 as well as in proximal direction 2. The drive member 70 is further threadedly engaged with the drive spindle 80. As illustrated in FIG. 13, the flange portion or rim 76 of the drive member 70 comprises an inner thread 79 engaging with an outer thread 81 of the drive spindle 80. Due to this threaded engagement and due to the axial fixing of the drive spindle 80 to the housing 20, a displacement of the drive member 70 in proximal direction 2 against the action of the spring element 78 comes along with a dose incrementing rotation 5 of the drive spindle 80.

Proximally-directed displacement of the drive member 70 relative to the housing 20 can be induced by a dose incrementing rotation of the dose setting member 50 and accordingly by a respective rotation of the gear wheel 58 and its sprocket 60. The axial length of the toothed rack portion 71 typically corresponds to the maximum distance the drive member 70 is allowed to be displaced in distal direction 1 according to the distance of the two stops 27 and 28.

Figure 4:
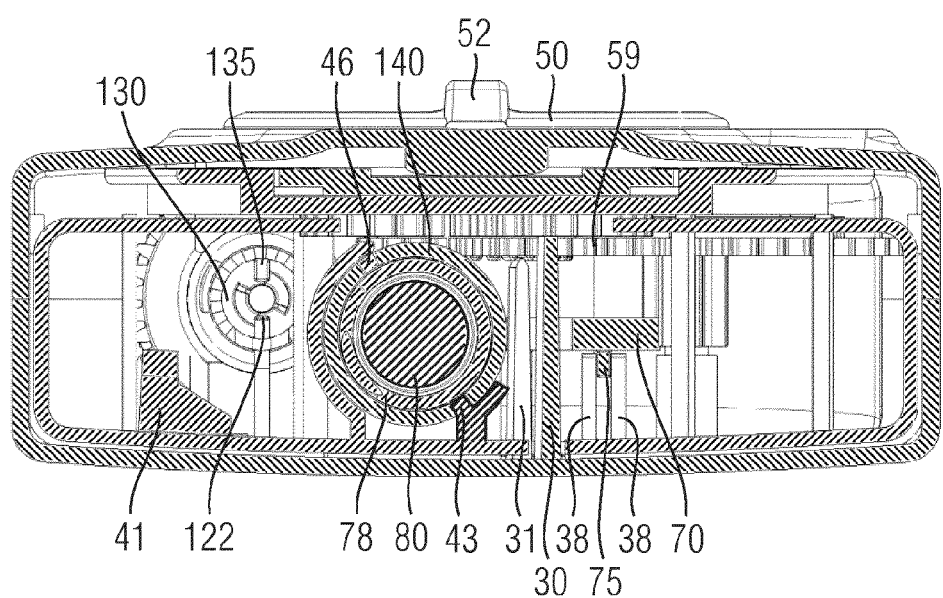
FIG. 4 shows a transverse cross-section through the drug delivery device according to A-A according to FIG. 2.

Additionally, as illustrated in FIGS. 4 and 15, there is provided a protruding ridge portion 75 on the side face of the toothed rack portion 71. Said ridge portion 75 can be guided in a guiding structure 38 of the housing 20 forming an elongated groove supporting the drive member 70 and guiding the drive member 70 in axial direction.

The toothed rack portion 71 comprises consecutive teeth 74 at its lateral side portion to engage with the sprocket 60 of the gear wheel 58.

Figure 9:
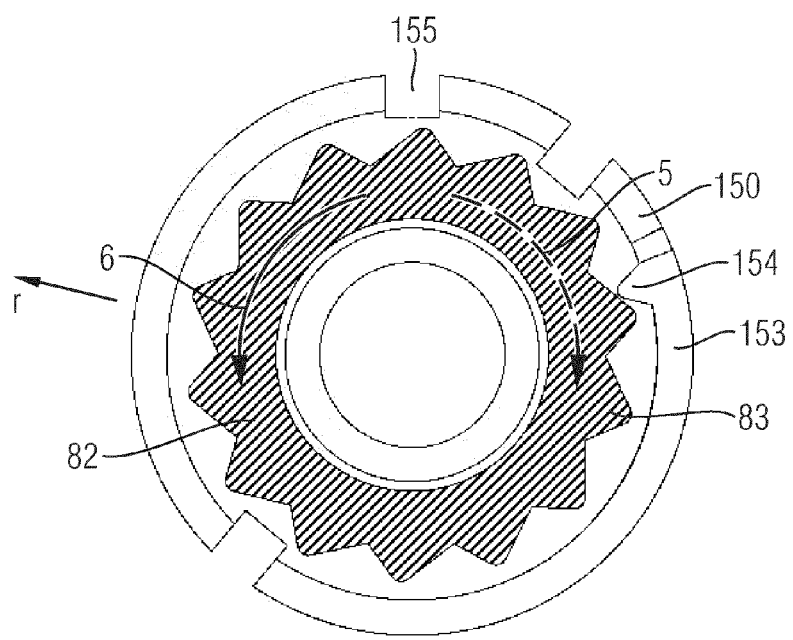
FIG. 9 shows a transverse cross-section B-B according to FIG. 2.

Drive member 70 and drive spindle 80 form a kind of a spindle gear. Proximally-directed displacement of the drive member 70 comes along with a tensioning of the spring element 78 thereby rotating the drive spindle 80 in a dose incrementing direction 5. The drive spindle 80 comprises a toothed rim 82 at its proximal end. As illustrated in cross-section of FIG. 9, said toothed rim 82 engages with a radially outwardly extending latch element 153 of a ratchet member 150. The cup-shaped ratchet member 150 receives the toothed rim 82 of the drive spindle 80 and inhibits a counter-directed, hence, a dose decrementing rotation 6 of the drive spindle 80.

For this purpose, the latch element 153 comprises an arc-shape and at least partially extends along the outer circumference of the toothed rim 82 of the drive spindle 80. The latch element 153 serves as a clutch element and the ratchet member 150 serves as a clutch member to selectively inhibit a rotation of the drive spindle 80. Typically, during dose setting, the latch or clutch element 153 meshes with a radially inwardly extending lug 154 with the teeth 83 of the toothed rim 82.

The latch element 153 is either pivotal in radial direction (r) and/or is resiliently deformable in radial direction to engage with the teeth 83 of the toothed rim 82 of the drive spindle 80. Depending on the slope and geometry of mutually engaging teeth 83 and the lug 154, a dose incrementing rotation 5 as well as a dose decrementing rotation 6 of the drive spindle 80 requires application of a respective actuation force above a predefined level or threshold.

The mutual engagement of the latch element 153 with the toothed rim 82 is in any case sufficient to counterbalance the relaxing force of a biased spring element 78. In this way, the ratchet member 150 is operable to keep the drive spindle 80 fixed, independent of the axial position of the drive member 70 and the degree of tension of the spring element 78.

The spring element 78 may abut with its proximal end at the radially outwardly extending toothed rim 82 of the drive spindle 80. In this way, the spring element 78 is axially constrained between the drive spindle 80 and the drive member 70.

Figure 20:
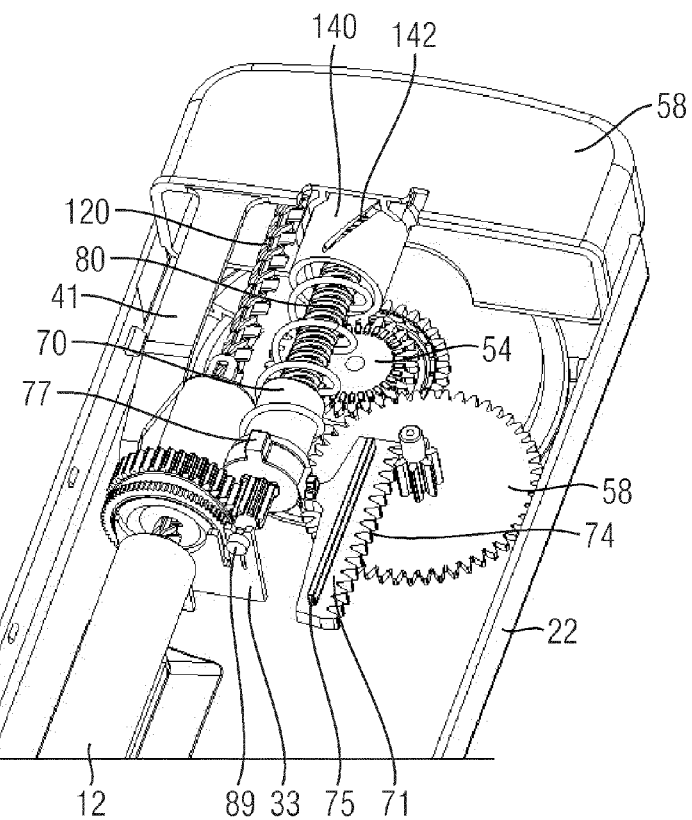

The distal end of the drive spindle 80 is provided with a pinion 86 featuring a bearing portion 89 in form of a circumferential groove or recess. As illustrated in FIGS. 13 and 20, the pinion 86 is supported by a bearing 33 of the housing 20, thereby axially and radially fixing the drive spindle 80 in the housing 20. The pinion 86 comprises various cogs or teeth 88 engaging with a geared rim 93 of a drive sleeve 90. The drive sleeve 90 as illustrated in detail in FIGS. 14 and 15 comprises a tubular-shaped sleeve portion and a radially extending flange portion 92 at its distal end.

The flange portion 92 is provided with a geared rim 93 that meshes with the pinion 86 of the drive spindle 80. Here, drive spindle 80 and drive sleeve 90 are permanently geared. Therefore, a dose incrementing as well as a dose decrementing rotation of the drive spindle 80 always leads to a corresponding rotation of the drive sleeve 90.

Furthermore, the drive sleeve 90 at least partially encloses the piston rod 120. The drive sleeve 90 is operably releasable from the piston rod 120 during dose setting but is operably engageable with the piston rod 120 for dispensing of a dose, as will be explained later on.

Figure 14:
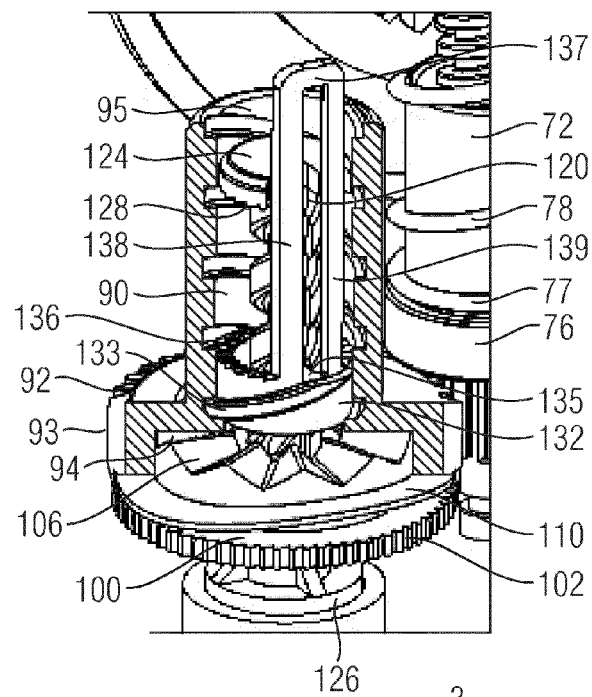
FIG. 14 is a partially cut- and enlarged view of the drive sleeve.

Radially sandwiched between the drive sleeve 90 and the piston rod 120 there is provided a dose limiting member 130. The dose limiting member 130 as illustrated in FIG. 14 comprises a sleeve portion 132 featuring an outer thread 133 engaged with an inner thread 95 of the drive sleeve 90. Moreover, the dose limiting member 130 comprises a proximally extending bracket portion 137 featuring two axially extending and parallelly-oriented branches 138, 139 that are mutually interconnected with their proximal ends to form a closed frame structure.

As illustrated for instance in FIG. 15, a proximal end of the bracket portion 137 extends in proximal direction from a proximal end of the drive sleeve 90. By means of the bracket portion 137, the dose limiting member 130 can be rotatably fixed to the housing 20.

For instance, a correspondingly extending pin that may e.g. radially extend from the housing 20 may protrude through the closed frame structure of the bracket portion 137 in radial direction, thereby effectively inhibiting that the dose limiting member 130 rotates as the drive sleeve 90 is set in rotation by means of the drive spindle 80. Due to the threaded engagement of the dose limiting member 130 and the drive sleeve 90 the dose limiting member 130 experiences a proximally-directed displacement relative to the drive sleeve 90 when the drive sleeve 90 is rotated in a dose incrementing direction 5.

Since a direct mechanical interaction or contact between the drive sleeve 90 and the piston rod 120 is not required, the dose limiting member 130 can be arranged inside the drive sleeve 90 in a rather contactless configuration relative to the piston rod 120, which also extends therethrough. Internal friction of the drive mechanism 3 can therefore be reduced.

Moreover and as illustrated in FIG. 14, the piston rod 120 comprises a stop member 124 which is adapted to engage with the dose limiting member 130 when a maximum number of doses has been dispensed by the drive mechanism 3. In the present embodiment, the stop member 124 of the piston rod 120 comprises a radially outwardly extending flange portion to engage with the proximally-located rim 136 of the sleeve portion 132 of the dose limiting member 130. Preferably, the faces of the stop member 124 and the sleeve portion 132 that face towards each other and which get in direct mutual contact when a last dose configuration is reached comprise a geared structure.

Hence, a distally-facing portion of the stop member 124 may comprise a geared flange, e.g. in form of a crown wheel 128. Correspondingly, also the proximal face of the sleeve portion 132 may comprise a geared rim or a crown wheel portion 136 to mate with the crown wheel 128 of the piston rod 120. Such a configuration may be beneficial with such embodiments, where the piston rod 120 rotates when it is driven in distal direction 1 during dose dispensing.

Mutually engaging crown wheels 128, 136 of the piston rod 120 and the dose limiting member 130 may then immediately inhibit any further rotation of the piston rod 120 relative to the rotatably fixed dose limiting member 130. Said mutual engagement is of particular benefit, when the complete content of the cartridge 12 has been expelled. Then, dose limiting member 130 and piston rod 120 are securely interlocked and effectively impede any further incrementing dose setting.

The dose limiting member 130 effectively serves as a last dose limiter. In an initial configuration of the drive mechanism 3 as for instance illustrated in FIG. 15, the dose limiting member 130 will travel in proximal direction 2 during a dose incrementing rotation of drive spindle 80 and drive sleeve 90. Since the dose setting of a single dose is limited by the axially confined displacement of the drive member 70, the dose limiting member 130 will at maximum reach a proximal end position, in which the sleeve portion 132 still remains in the drive sleeve 90.

In such a configuration the dose limiting member 130 will be separated from the stop member 124 of the piston rod 120. During a consecutive dose dispensing action, the piston rod 120 will advance in distal direction 1 relative to the drive sleeve 90. Since a distally-directed dispensing displacement of the piston rod 120 comes along with a dose decrementing rotation of the drive sleeve 90, also the dose limiting member 130 will return into its initial zero dose configuration as for instance illustrated in FIG. 14.

There may be provided a stop member inside the drive sleeve 90 to provide a well-defined distal stop for the dose limiting member 130. However, such a zero dose stop is not necessarily required for the dose limiting member 130 since the dose decrementing rotation 6 of the drive sleeve 90 is already delimited by the drive member 70 engaging with a distal stop 28 of the housing 20.

With a consecutive dose setting procedure, the dose limiting member 130 will repeatedly displace in axial direction 2. Since the piston rod 120 has moved in distal direction 1 during the previous dose dispensing procedure, the stop member 124 of the piston rod 120 continuously approaches to the axial range in which the dose limiting member 130 is displaceable. If the position of the piston rod 120 corresponds to a dose size smaller than the maximum size of a single dose, e.g. smaller than 120 I.U., the stop member 124 of the piston rod 120 may enter the drive sleeve 90 as for instance illustrated in FIG. 14.

In a proceeding dose setting procedure, the dose incrementing rotation of the drive sleeve 90 is immediately stopped, when the proximally-advancing dose limiting member 130 axially engages with the stop member 124 of the piston rod 120. In this way, it can be assured, that the sum of consecutive doses set and dispensed does not exceed the total amount of doses of the medicament contained in the cartridge 12.

The stop member 124 may comprise a lateral recess in order to receive and to pass by the bracket portion 137 of the dose limiting member 130. Additionally or alternatively, it is also conceivable, that the dose limiting member 130 is splined to the piston rod 120 itself. As for instance illustrated in FIG. 4, the dose limiting member 130 may comprise a radially inwardly extending protrusion 135 to engage with an axially extending groove 122 of the piston rod 120. In this way, the dose limiting member 130 can be rotatably locked to the piston rod 120. In such an alternative embodiment, the piston rod 120 should be rotatably fixed to the housing. Here, the piston rod 120 could be splined to the housing 20.

In the following dispensing of a dose will be described.

Figure 16:
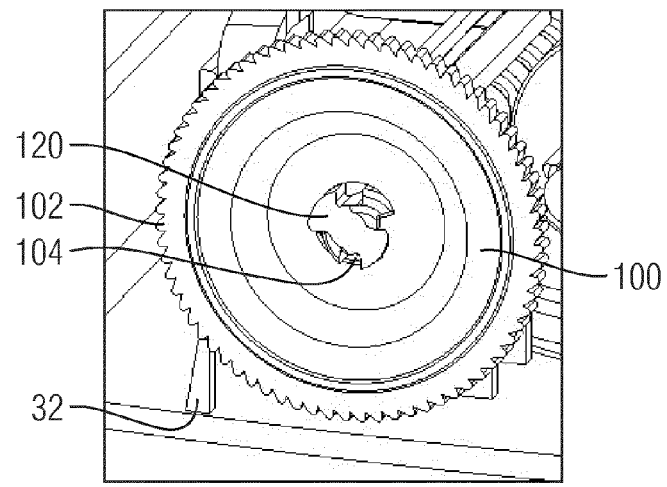
FIG. 16 shows a perspective view of a drive wheel engaged with the piston rod.

For dispensing of a dose the drive sleeve 90 rotates in a dose decrementing direction 6 in such a way, that the torque of the drive sleeve 90 is transferred to a distally-directed displacement of the piston rod 120. As illustrated in FIG. 14, the drive sleeve 90 is coaxially aligned with a drive nut or drive wheel 100. The drive wheel 100 comprises a radially outwardly extending geared rim 102. The teeth of said rim 102 comprise a saw tooth profile and engage with a ratchet member 32 of the housing 20 as illustrated in FIG. 16.

By means of the mutual engagement of the ratchet member 32 with the geared rim 102 rotation of the drive wheel 100 is only allowed in a dose dispensing or dose decrementing direction. A counter-directed movement is effectively blocked and inhibited by said engagement. Moreover, during a dose decrementing or dose dispensing rotation of the drive wheel 100, the ratchet member 32 generates an audible click sound thereby providing an audible feedback to the user, that the injection or dose dispensing is in progress.

The drive wheel 100 further comprises a through opening to receive the piston rod 120 therethrough. The piston rod comprises an outer thread 121 and/or a longitudinally extending groove 122. By means of a groove 122 the piston rod 120 could be rotatably fixed to the housing 20. By means of a threaded engagement of the piston rod 120 with an inner thread 104 of the drive wheel 100, the rotation of the axially fixed drive wheel 100 can be transferred into a distally-directed displacement of the piston rod 120.

In an alternative but not illustrated embodiment, it is also conceivable, that the piston rod 120 is splined to the drive wheel 100 and that the piston rod 120 is threadedly engaged with a housing portion. In such a technically equivalent configuration, rotation of the drive wheel 100 equally transfers into a distally-directed displacement of the piston rod 120 relative to the housing 20 and relative to the barrel of the cartridge 12.

A torque to rotate the drive wheel 100 is provided by the drive sleeve 90, which is axially displaceable between a proximal stop position, in which the drive sleeve 90 is decoupled or disengaged from the drive wheel 100 and hence from the piston rod 120. In its distal stop position, the drive sleeve 90 operably engages with the drive wheel 100 in a torque transmissive way.

As for instance illustrated in FIG. 15, the drive sleeve 90 comprises a radially outwardly extending flange portion 92 at its distal end. From said flange portion 92, there extends a geared rim 93 radially outwardly. The distal end face of the geared rim comprises a ring structure to mate with a correspondingly-shaped flange portion of drive wheel's geared rim 102. Between the rim 102 and the rim 93 there is provided a disc spring 110 which serves to displace the drive sleeve 90 in proximal direction 2.

Hence, drive sleeve 90 and drive wheel 100 can be axially coupled against the action of the disc spring 110 positioned there between. The rim portions 93, 102 of drive sleeve 90 and drive wheel 100 carrying and supporting the disc spring 110 are substantially flat-shaped. In order to transfer angular momentum between the drive sleeve 90 and the drive wheel 100 the drive sleeve 90 comprises a crown wheel portion 94 radially inwardly from the geared rim 93. Correspondingly, the drive wheel 100 comprises a proximally extending socket featuring a correspondingly-shaped crown wheel 106.

When the drive sleeve 90 is displaced in distal direction 1 to get in direct contact with the drive wheel 100, said crown wheels 94, 106 mutually engage and angular momentum acting on the drive sleeve 90 may equally transfer to the drive wheel 100, thereby leading to a distally-directed displacement of the piston rod 120. A distally-directed displacement of the drive sleeve 90 against the action of the disc spring 110 is inducible by a dose dispensing button 40 provided at a proximal end of the housing 20.

Figure 17:
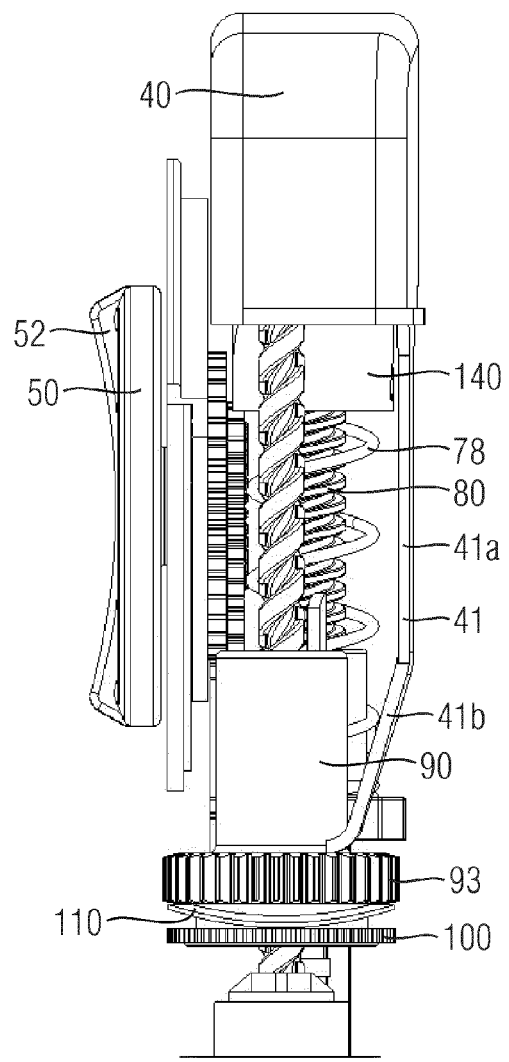
FIG. 17 shows an isolated side view of the drive mechanism without the housing, FIG. 18 schematically shows the mutual interaction of the drive spindle with the drive sleeve.
Figure 18:
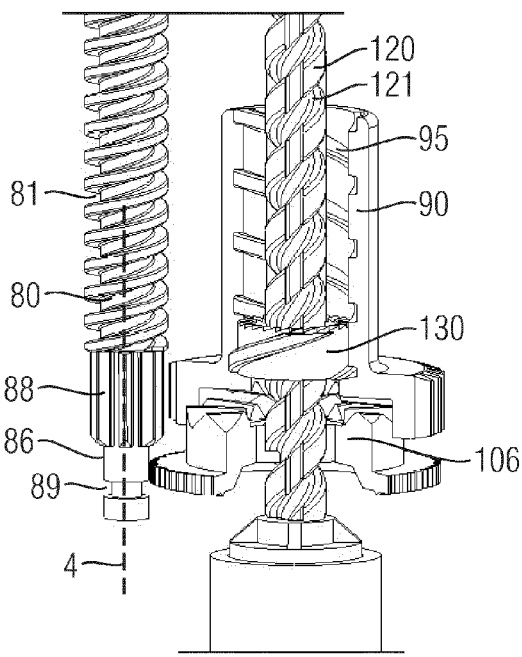
Figure 19:
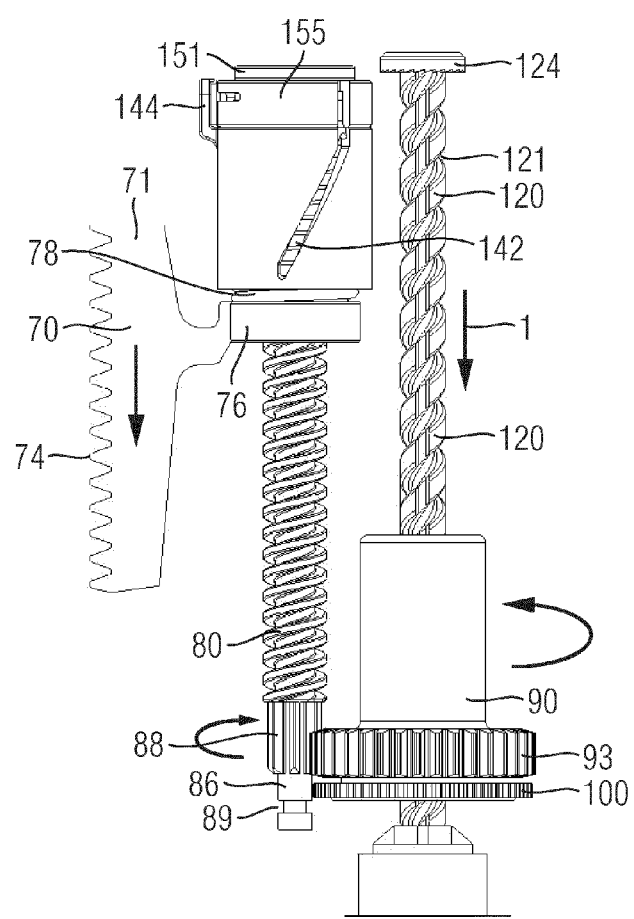
FIG. 19 shows a configuration of the drive mechanism with the drive member in its proximal stop position, FIG. 20 schematically illustrates the assembly of the drive mechanism inside a lower housing portion.

As for instance illustrated in FIG. 17, the dose dispensing button 40 comprises a distally extending strut 41 to but against a proximal-facing portion of the radially outwardly extending flange portion 92 of the drive sleeve 90. The strut 41 comprises a proximal rather axially extending strut portion 41a and a distal strut portion 41b which extends at a predefined angle with respect to the axial direction. In this way, the strut 41 is at least resiliently deformable to a certain degree so that a clutch between the drive sleeve 90 and the drive wheel 100 remains engaged even when the position of the dose dispensing button 40 in axial direction varies to a certain extent.

Depression of the dose dispensing button 40 in distal direction 1 not only engages the drive sleeve 90 and the drive wheel 100. Additionally, distally-directed displacement of the dose dispensing button 40 leads to a release of the drive spindle 80 relative to the ratchet member 150.

Figure 21:
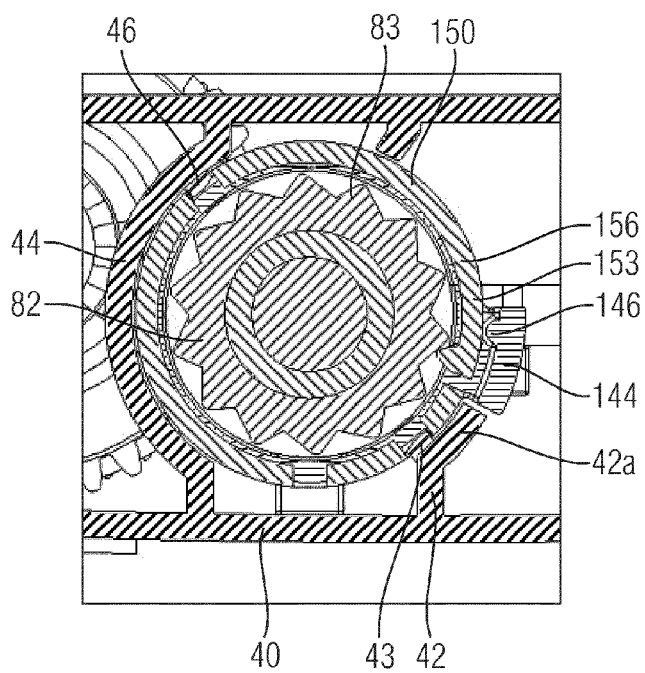
FIG. 21 shows a cross-section along B-B together with the dose dispensing button.
Figure 23:
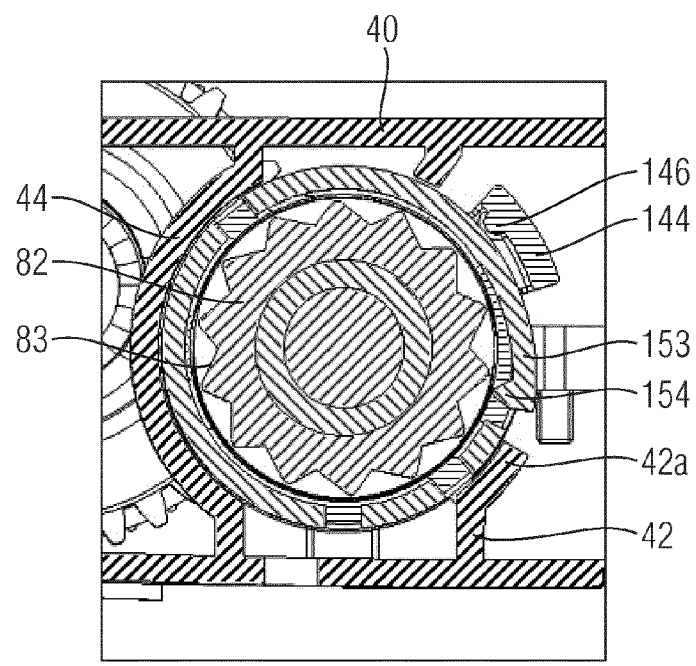
FIG. 23 shows a cross-section B-B according to FIG. 2 with the regulating member in a release configuration.

As becomes apparent from a comparison of FIGS. 21 and 23, the latch element 153 is resiliently deformable in radial direction. As shown in the released configuration according to FIG. 23, the latch element 153 radially protrudes from the outer circumference of the sidewall 156 of the cup-shaped ratchet member 150. In this configuration, the radially inwardly extending lug 154 provided at the free end of the resiliently deformable latch element 153 is no longer engaged with the teeth 83 of the toothed rim 82 of the drive spindle 80.

In the released configuration the drive spindle 80 is effectively free to rotate under the action of the relaxing spring element 78 and the spindle gear of drive spindle 80 and drive member 70 which is driven by said spring element 78.

In the locked or engaged configuration according to FIG. 21, the arc-shaped latch element 153 is biased radially inwardly so that its radially inwardly extending lug 154 engages with the teeth 83 of the drive spindle 80. Radially-directed displacement of the latch element 153 is governed by a biasing member 144 provided at a proximal end of a sleeve-shaped regulating member 140.

Figure 22:
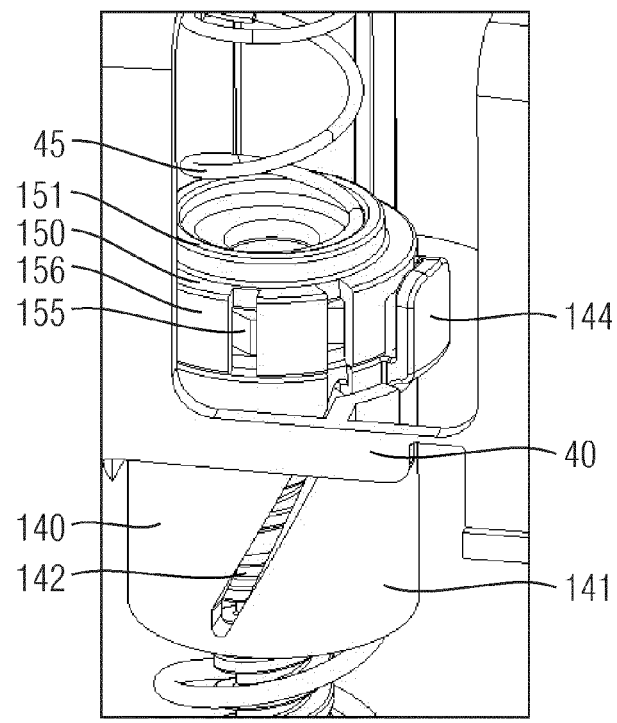
FIG. 22 shows an enlarged perspective view of the mutual engagement of the dose setting button with a regulating member.
Figure 24:
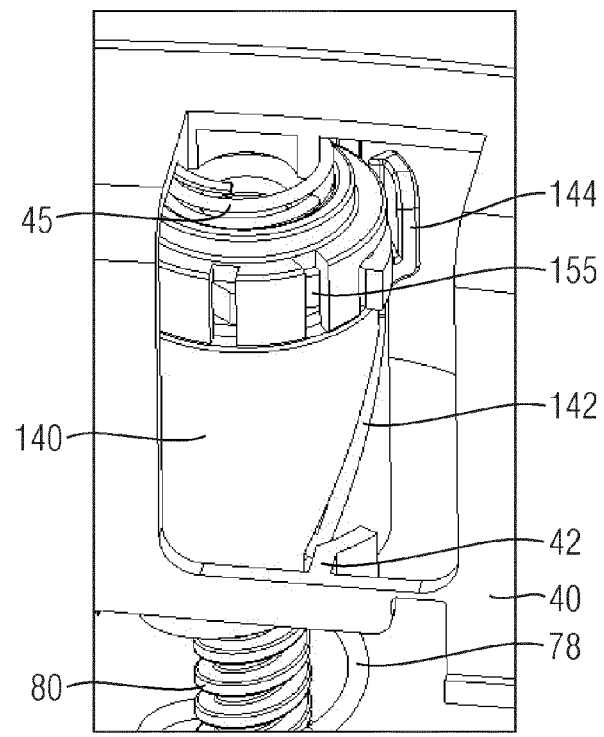
FIG. 24 shows a perspective view according to FIG. 22 with the dose dispensing button fully depressed.

The regulating member 140 is rotatably and coaxially arranged to the ratchet member 150 as for instance illustrated in FIGS. 22 and 24. The regulating member 140 comprises a sleeve portion 141 featuring at least one inclined slit 142 or a respective groove on its outer circumference. As illustrated in FIG. 21 the dose dispensing button 40 comprises an inwardly extending guiding member 42 featuring a radially inwardly extending pin 43 engaging with the inclined slit 142 of the regulating member 140.

Due to the inclined orientation of the slit 142 relative to the axial direction, a distally-directed displacement of the dose dispensing button 40 leads to continuous rotation of the regulating member 140. As a consequence, the biasing member 144 travels along the outer circumference of the arc-shaped latch element 153. Here, the biasing member 144 comprises a radially inwardly extending bulged portion 146 which abuts with an outer circumference of the arc-shaped latch element 153.

In the interlocked configuration, which corresponds to the dose dispensing button 40 in its proximal stop position, the biasing member 144 is fairly close to the free end of the arc-shaped latch element 153. A depression of the dose dispensing button 40 in distal direction 1 comes along with a corresponding rotation of the regulating member 140 and leads to a continuous displacement of the biasing member 144 along the outer circumference of the arc-shaped latch element 153.

As a consequence and as illustrated in FIG. 23, the free end of the latch element 153 may extend radially outwardly. Due to the engagement of the guiding member 42 of the dose dispensing button 40 with the inclined slit 142 of the regulating member 140, the degree of rotation of the regulating member 140 and its biasing member 144 is directly correlated to the degree of axial depression of the dose dispensing button 40.

Due to the resiliently deformable properties of the arc-shaped latch element 153, the holding force provided by the latch element 153 and acting on the toothed rim 82 of the drive spindle 80 can be continuously and steplessly reduced or modified. In this way, mutual friction and gliding behaviour of the latch element 153 and the toothed rim 82 of the drive spindle 80 can be modified in dependence of the depth or degree of axial depression of the dose dispensing button 40.

Depending on the degree of rotation of the regulating member 140, the holding force acting on the drive spindle 80 during an injection procedure can be continuously modified, thereby allowing to regulate the angular velocity of the drive spindle 80 when rotating in a dose decrementing, hence in a dose dispensing orientation 6.

It is to be mentioned here, that the dispensing velocity regulation provided by the mutual interaction of drive spindle 80 and ratchet member 150 can be realized in a variety of different ways. The orientation of the drive spindle 80 serving as a rotatable member and/or the concrete mechanical interaction between the drive spindle 80 and the ratchet member 150 may vary from the illustrated embodiment.

It is only required that the ratchet member 153, generally serving as a clutch member 153, is at least partially radially displaceable with respect to the orientation of the axis of rotation 4 of the drive spindle 80 or of a respective rotatable element 80. Moreover, the mutual retarding interaction of ratchet member 150 and drive spindle 80 can be frictionally based. Additionally, a positive engagement of ratchet member 150 and drive spindle 80 may also exhibit a combined friction-based and positively engaging interaction.

As further illustrated by a comparison of FIGS. 22 and 24, the dose dispensing button 40 is coupled with the proximal end of the ratchet member 150 by means of a spring element 45, e.g. an injection spring 45, typically designed as a compression spring. As further illustrated in FIG. 21 the dose dispensing button 40 is intersected by a strut 44 having a half shell shape which at least partially adopts the outer circumference of the ratchet member 150. In the half shell-shaped portion the strut 44 further comprises an additional pin 46 to engage with a further slit 142 of the regulating member 140.

The regulating member 140 may therefore comprise two oppositely disposed slits 142 to engage with correspondingly arranged radially inwardly extending pins 43, 46 of the dose dispensing button 40. The inwardly extending guiding member 42 of the dose dispensing button 40 further comprises an outer guiding portion 42a, which also adopts the outer shape of the ratchet member 150. By means of the outer guiding portion 42a and the half shell strut 44, the dose dispensing button 40 can be axially guided along the ratchet member 150.

For a secure fastening of the spring element 45, the proximal end of the ratchet member 150 comprises a stepped portion 151 to receive the spring element 45 therein.

As becomes further apparent from FIGS. 21 and 22, the ratchet member 150 comprises axially extended notches 155 that allow to guide the radially inwardly extending pins 43, 46 of the dose dispensing button 40 past the ratchet member 150 during final assembly of the drive mechanism 3.

Depression of the dose dispensing button 40 in distal direction 1 for dispensing of a dose may then be divided into two consecutive steps. In a first step the dose dispensing button 40 is displaced in distal direction by a distance so that the pins 43, 46 advance in distal direction 1 into the slits 142 of the regulating member 140. During this initial displacement the axially extending strut 41 already serves to mutually engage the drive sleeve 90 and the drive wheel 100.

In this way, a torque transmissive coupling of the drive sleeve 90 with the piston rod 120 can be attained even before the drive spindle 80 and hence the drive member 70 are released from the ratchet member 150. It is only due to a further depression of the dose dispensing button 40 in distal direction 1, that the pins 43, 46 run along the slit or groove 142 leading to a releasing rotation of the regulating member 140 and to a gradual and continuous release of the latch element 153. The torque transmissive coupling of drive sleeve 90 and piston rod prior to a release of the drive spindle 80 from the ratchet member can be controlled and governed by the flexural behaviour and by the geometric design of the latch element 153. As already explained above, the depth of depression of the dose dispensing button 40 may determine or may at least influence the angular velocity of the drive spindle 80 during dose dispensing.

Under the action of the relaxing spring element 78, the drive member 70 will return into its initial zero dose configuration. Since the toothed rack portion 71 of the drive member 70 is geared with the sprocket 60 of the gear wheel 58, the dose indicating wheel 54, 56 will count down accordingly. Just before approaching an initial zero dose configuration, the drive member 70 may audibly engage with a clicking member 36 of the housing 20.

Figure 26:
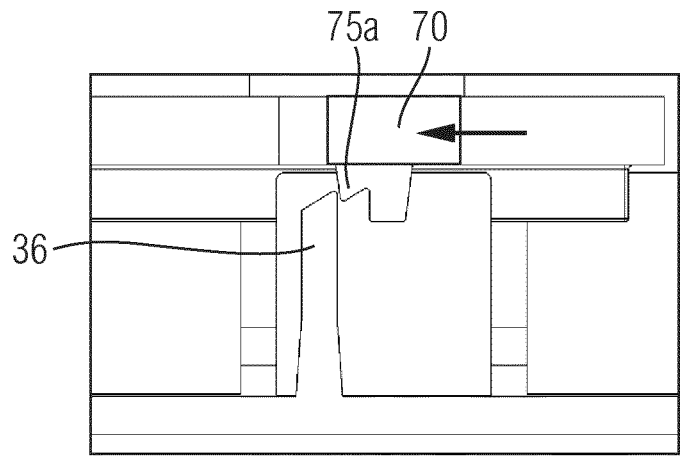
FIG. 26 shows a longitudinal cross-section of the drive member before reaching a zero dose configuration and FIG. 27 is indicative of the drive member reaching the zero dose configuration.
Figure 27:
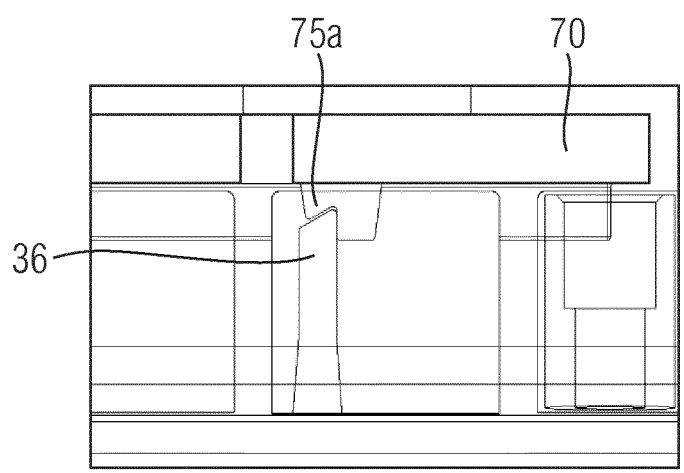

As shown in FIG. 26, the drive member 70 comprises a ledge 75a to engage with an inwardly extending pin-like clicking member 36. Just before reaching a zero dose configuration at the end of a dose dispensing procedure, the bevelled ledge 75a engages with the correspondingly bevelled clicking member 36, thereby generating an audible click sound, in particular when the resiliently deformable clicking member 36 returns into an initial abutment configuration with the bevelled ledge 75a as illustrated in FIG. 27. This audible feedback indicates to the user that a dispensing procedure has terminated.

LIST OF REFERENCE NUMERALS 1 distal direction
2 proximal direction
3 drive mechanism
4 axis of rotation
5 dose incrementing direction
6 dose decrementing direction
10 drug delivery device
12 cartridge
14 piston
15 needle assembly
16 needle hub
17 needle cap
20 housing 21 upper housing portion
22 lower housing portion
23 cartridge window
24 cap
25 socket
26 dose indicating window
27 proximal stop
28 distal stop
29 receptacle
29a slit
30 clicking member
31 clicking member
32 ratchet member
33 bearing
36 clicking member
37 fixing rim
38 guiding structure
40 dose dispensing button
41 strut
41a proximal strut portion
41b distal strut portion
42 guiding member
42a outer guiding portion
43 pin
44 strut
45 spring element
46 pin
50 dose setting member
51 receptacle
52 gripping bar
53 crown wheel
54 dose indicating wheel
55 sprocket
56 dose indicating wheel
57 geared rim
57a crown wheel
58 gear wheel
59 geared rim
60 sprocket
61 ring structure
62 cog
70 drive member
71 toothed rack portion
72 sleeve portion
73 bar
74 tooth
75 ridge portion
75a ledge
76 rim
77 protrusion
78 spring element
79 inner thread
80 drive spindle
81 outer thread
82 toothed rim
83 tooth
84 pinion
88 tooth
89 bearing portion
90 drive sleeve
92 flange portion
93 geared rim
94 crown wheel
95 inner thread
100 drive wheel
102 geared rim
104 inner thread
106 crown wheel
110 disc spring
120 piston rod
121 thread
122 groove
124 stop member
126 pressure piece
128 crown wheel
130 dose limiting member
132 sleeve portion
133 outer thread
135 protrusion
136 geared rim
137 bracket portion
138 branch
139 branch
140 regulating member
141 sleeve portion
142 slit
144 biasing member
146 bulged portion
150 ratchet member
151 stepped portion
153 latch element
154 lug
155 notch
156 sidewall

The invention claimed is:

1. A drive mechanism of a drug delivery device for dispensing of a dose of a medicament, the drive mechanism comprising:
    a housing;
    a piston rod extending in an axial direction to operably engage with a piston of a cartridge;
    a drive sleeve rotatably supported in the housing, at least partially enclosing the piston rod, wherein the drive sleeve is operably releasable from the piston rod for setting of a dose and is operably engageable with the piston rod for dispensing of the dose;
    a dose limiting member threadedly engaged with the drive sleeve, rotatably locked to the housing, and displaceable in the axial direction in response to a rotation of the drive sleeve relative to the piston rod; and
    at least one stop member provided on the piston rod to engage with the dose limiting member for impeding a further displacement of the drive sleeve relative to the piston rod when a maximum dose configuration has been reached;
    wherein the dose limiting member comprises at least one radially inwardly extending protrusion engaged with a correspondingly shaped and axially extending groove of the piston rod.

2. The drive mechanism according to claim 1, wherein the dose limiting member is arranged radially between the drive sleeve and the piston rod.

3. The drive mechanism according to claim 1, wherein the dose limiting member comprises a sleeve portion enclosing the piston rod.

4. The drive mechanism according to claim 3, wherein the sleeve portion comprises an outer thread engaged with an inner thread of the drive sleeve.

5. The drive mechanism according to claim 1, wherein the dose limiting member comprises a bracket portion extending in the axial direction and at least partially protruding from a proximal end of the drive sleeve.

6. The drive mechanism according to claim 5, wherein the bracket portion comprises two axially extending and parallel oriented branches being mutually interconnected to form a closed frame structure operable to slidably receive a pin of the housing therein.

7. The drive mechanism according to claim 1, wherein the at least one stop member comprises a radially outwardly extending flange portion at a proximal end of the piston rod.

8. The drive mechanism according to claim 1, wherein the at least one stop member comprises a crown wheel facing in a distal direction to mate with a correspondingly geared proximal rim of the dose limiting member.

9. The drive mechanism according to claim 1, wherein the drive sleeve is axially displaceable in a distal direction against the action of a spring, which is axially sandwiched between a proximal rim of the drive sleeve and a drive wheel rotatably engaged with the piston rod.

10. The drive mechanism according to claim 9, wherein the drive wheel is threadedly engaged with the piston rod.

11. The drive mechanism according to claim 9, wherein the drive sleeve comprises a crown wheel portion at a distal end face to mate with a correspondingly shaped crown wheel portion of the drive wheel.

12. The drive mechanism according to claim 9, wherein the proximal rim of the drive sleeve is geared with a pinion of a drive spindle rotatably supported in the housing in a dose incrementing direction against the action of the spring.

13. The drive mechanism according to claim 9, wherein the drive wheel comprises a geared rim engaged with a ratchet member of the housing operable to generate an audible click sound when the drive wheel rotates in a dose dispensing direction and being further operable to impede a rotation of the drive wheel in the opposite direction.

14. A drug delivery device for setting and dispensing of a dose of a medicament, the drug delivery device comprising:

a drive mechanism comprising:
  a housing,
  a piston rod extending in an axial direction to operably engage with a piston of a cartridge,
  a drive sleeve rotatably supported in the housing, at least partially enclosing the piston rod, wherein the drive sleeve is operably releasable from the piston rod for setting of a dose and is operably engageable with the piston rod for dispensing of the dose,
  a dose limiting member threadedly engaged with the drive sleeve, rotatably locked to the housing, and displaceable in the axial direction in response to a rotation of the drive sleeve relative to the piston rod, and
  at least one stop member provided on the piston rod to engage with the dose limiting member for impeding a further displacement of the drive sleeve relative to the piston rod when a maximum dose configuration has been reached, wherein the dose limiting member comprises at least one radially inwardly extending protrusion engaged with a correspondingly shaped and axially extending groove of the piston rod; and
a cartridge containing the medicament and being arranged in the housing of the drive mechanism.

15. The drug delivery device according to claim 14, wherein the dose limiting member is arranged radially between the drive sleeve and the piston rod.

16. The drug delivery device according to claim 14, wherein the dose limiting member comprises a sleeve portion enclosing the piston rod.

* * * * *

UNITED STATES PATENT AND TRADEMARK OFFICE
CERTIFICATE OF CORRECTION

| | | |
|---|---|---|
| PATENT NO. | : 10,226,581 B2 | Page 1 of 1 |
| APPLICATION NO. | : 14/783190 | |
| DATED | : March 12, 2019 | |
| INVENTOR(S) | : Stefan Bayer et al. | |

It is certified that error appears in the above-identified patent and that said Letters Patent is hereby corrected as shown below:

On the Title Page

Item (56), Column 2 (Other Publications), Line 1, delete "Hypophyses-," and insert
-- Hypophysen-, --.

Signed and Sealed this
Twenty-fifth Day of June, 2019

Andrei Iancu
*Director of the United States Patent and Trademark Office*